US007226745B2

(12) United States Patent
Cahoon et al.

(10) Patent No.: US 7,226,745 B2
(45) Date of Patent: Jun. 5, 2007

(54) PLANT VITAMIN E BIOSYNTHETIC ENZYMES

(75) Inventors: Rebecca E. Cahoon, Wilmington, DE (US); Sean J. Coughlan, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/141,593

(22) Filed: May 31, 2005

(65) Prior Publication Data

US 2005/0216973 A1     Sep. 29, 2005

Related U.S. Application Data

(62) Division of application No. 09/857,613, filed as application No. PCT/US99/28588 on Dec. 2, 1999, now Pat. No. 7,071,381.

(60) Provisional application No. 60/110,781, filed on Dec. 3, 1998.

(51) Int. Cl.
*A01H 1/00*   (2006.01)
*C07H 21/04*  (2006.01)
*C07K 14/415* (2006.01)
*C12N 5/10*   (2006.01)
*C12N 9/00*   (2006.01)

(52) U.S. Cl. .................. 435/6; 435/69.1; 435/70.1; 435/183; 435/235; 435/410; 435/419; 435/252.3; 435/320.1; 530/370; 536/23.2; 536/23.6; 536/24.1; 800/278; 800/298

(58) Field of Classification Search .................. None
See application file for complete search history.

(56) References Cited

FOREIGN PATENT DOCUMENTS

WO     WO 99/04622 A1    2/1999

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
EMBL Sequence Database Library Accession No. D64004, Oct. 4, 1995, Synechocystis sp. PCC6803 complete genome, delta (24) sterol C-methyltransferase.
G.E. Bartely et al., Plant Phys., vol. 113:1465, 1997, Cloning of an *Arabidopsis thaliana* cDNA for p-hydroxyphenylpyruvate dioxygenase.
D. Shintani et al. Abstract of the oral presentation at the annual meeting of The American Society of Plant Physiology, Jun. 28, 1998, A New Paradigm for plant biochemistry: Nutritional genomics, Vitamin E. synthesis and human nutrition as an example.
David Shintani et al., Science, vol. 282(5396):2098-2100, 1998, Elevating the vitamin E content of plants through metabolic engineering.
Susan R. Norris et al., Plant Cell, vol. 7:2139-2149, 1995, Genetic dissection of cartenoid synthesis in *Arabidopsis* defines plastoquinone as an essential component of phytoene desaturation.
Isabelle Garcia et al., Biochem. J., vol. 325:761-769, 1997, Subcellular localization and purification of a p-hydroxyphnlpyruvate dioxygenase from cultured carrot cells and characterization of the corresponding cDNA.
David J. Mayonado et al., Pesticide Biochem. & Phys., vol. 35:138-145, 1989, Evaluation of the mechanism of action of the bleaching herbicide SC-0051 by HPLC Analysis.
Arno Schulz et al., FEBS Letters, vol. 318(2):162-166, 1993, SC-0051, a 2-benzoyl-cyclohexane-1,3 dione bleaching herbicide, is a potent inhibitor of the enzyme p-hydroxyphenylpyruvate dioxygenase.
Jacob Secor, Plant Phys., vol. 106:1429-1433, 1994, Inhibition of Bamyardgrass 4-Hydroxyphenylpyruvate Dioxygenase for Sulcotrione.
National Center for Biotechnology Information General Identifier No. 1001725, Jul. 4, 2001, T. Kaneko et al. Sequence Analysis of the genome of the unicellular Cyanobacterium Synchocystis sp. strain PCC6803. I Sequence features in the 1 Mb region from map positions 64% to 92% of the genome.
Takakazu Kaneko et al., DNA Res., vol. 2:153-166, 1995, Sequence analysis of the genome of the unicellular cyanobacterium Synechocystis sp. strain, PCC6803. I Sequence features in the 1 Mb region from map postions 64% to 92% of the genome.
Takakazu Kaneko et al., DNA Res., vol. 3:109-136, 1996, Sequence analysis of the genome of the unicellular cyanobacterium Synechocystis sp. Strain PCC6803 II. Sequence determination of the Entire genome and assignment of potential protein-coding regions.
National Center for Biotechnology Information General Identifier No. 4106538, Jan. 5, 1999, D.K. Shintani et al., Elevating vitamin E content of plants through metabolic engineering.
National Center for Biotechnology Information Identifier No. 3334222, Aug. 20, 2001, K. Krupinska et al.
National Center for Biotechnology for Biotechnology Information General Identifier No. 3334219, Aug. 20, 2001, I. Garcia et al., Subcellular localization and purification of a p-hydroxyphenlpyruvate dioxygenase from cultured carrot cells and characterization of the corresponding cDNA.
National Center for Biotechnology Information Identifier No. 3334223, Aug. 20, 2001, S.R. Norris et al.
Alain D'Harlingue et al., Journ. of Biol. Chem, vol. 260(28):15203, 1985, Plastid enzymes of terpeniod biosynthesis.
Kagan, R.M. et al., "Widespread Occurrence of Three Sequence Motifs in Diverse S-Adenosylmethionine-Dependent Methyltransferases Suggests a Common Structure for These Enzymes," Archives of Biochemistry and Biophysics, May 1, 1994, pp. 417-427, vol. 310, No. 2.
Willcock, D.F. et al., "A mutational analysis of the two motifs common to adenine methyltransferases," The EMBO Journal, 1994, pp. 3902-3908, vol. 13, No. 16.
Joshi, Chandrashekhar P. et al., "Conserved Sequence Motifs in Plant S-Adenosyl-L-Methionine-Dependent Methyltransferases", Plant Molecular Biology, 1998, pp. 663-674, vol. 37.

* cited by examiner

*Primary Examiner*—Phuong T Bui
*Assistant Examiner*—Vinod Kumar

(57) ABSTRACT

This invention relates to an isolated nucleic acid fragment encoding a vitamin E biosynthtetic enzyme. The invention also relates to the construction of a chimeric gene encoding all or a portion of the vitamin E biosynthtetic enzyme, in sense or antisense orientation, wherein expression of the chimeric gene results in production of altered levels of the vitamin E biosynthtetic enzyme in a transformed host cell.

11 Claims, 7 Drawing Sheets

FIGURE 1A

Figure 3:
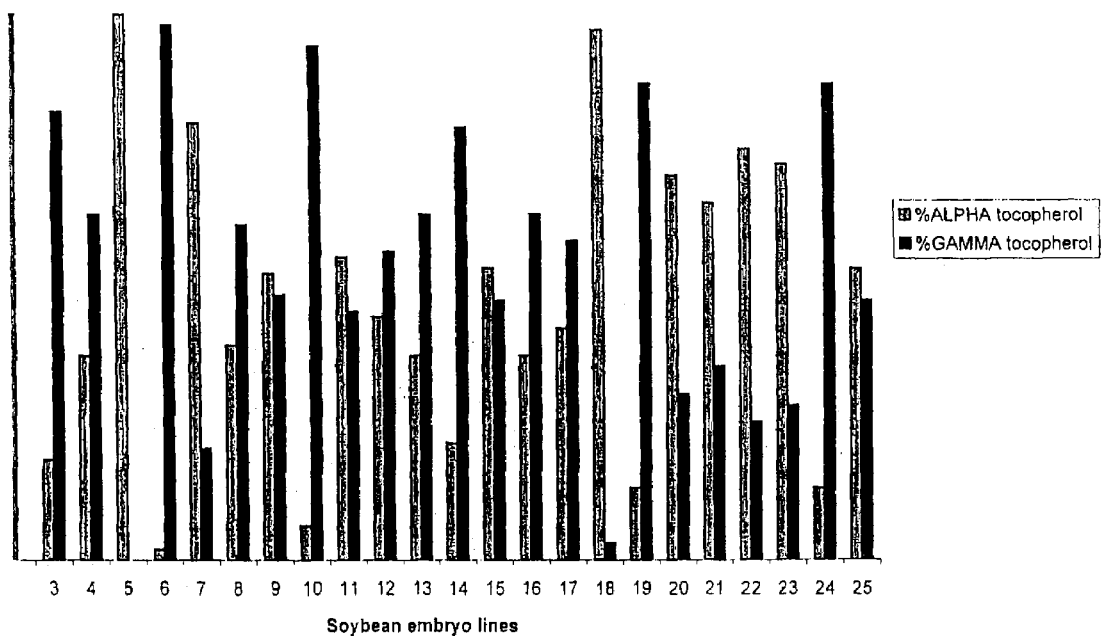

```
SEQ ID NO:39   MVYHVRPKHAL------------FLAFYCYFS---------------------------------
SEQ ID NO:40   MKATLAAPSSLTSL-P-------YRTNSS-FGSKSSLLFRSPSSSSVS-MTTTRGNV
SEQ ID NO:38   MAN-------SXRPA-PLTPLHRLDAAPPPRPSLGHAARPVPRPVLPLLPAR-XLRAPDGV
SEQ ID NO:28   MATVVRI--------PTISCIHIHTFRSQSPRTFARIRVGPRSWAPIRASA-ASSERGEI
SEQ ID NO:08   MATVVRI--------PTISCIHIHTFRSQSPRTFARIRVGPRSWAPIRASA-ASSERGEI
SEQ ID NO:22   MAHAALLHCSQSSR-SLAACRRGSHYRAPSH-VPRHSRLRRAVVSL--R-PMASSTA-
SEQ ID NO:24   AR--VQPTGALAPLHPLLRCTSRHLCASASPRAGLCLHHHRRRRSSRRTKLAVRAMAPT
SEQ ID NO:26   FRH-------GH----------------------------------AL---------
                1                                                              60

SEQ ID NO:39   LLTMASATIASADLYEKIKNFYDDSSGLWEDVWGEHMHHGYYGPHGTYRI---DRRQAQI
SEQ ID NO:40   AVAAAATSTEA--LRKGIAEFYNETSGLWEEIWGDHMHHGFYDPDSSVQLSDSGHKEAQI
SEQ ID NO:38   VDDRGPGDAAPPGLKEGIAGLYDESSGLWESIWGEHMHHGFYDSGEAASMSD--HRRAQI
SEQ ID NO:28   VLEQKPKKDDKKKLQKGIAEFYDESSGLWENIWGDHMHHGFYDSDSTVSLSD--HRAAQI
SEQ ID NO:08   VLEQKPKKDDKKKLQKGIAEFYDESSGLWENIWGDHMHHGFYDSDSTVSLSD--HRAAQI
SEQ ID NO:22   ---QAPATAPPGLKEGIAGLYDESSGLWENIWGDHMHHGFYDSSEAASMAD--HRRAQI
SEQ ID NO:24   LSSSSTAAAAPPGLKEGIAGLYDESSGVWESIWGEHMHHGFYDAGEAASMSD--HRRAQI
SEQ ID NO:26   ----------------------------------------------------------
                61                                                             120

SEQ ID NO:39   DLIKELLAWAVPQNSA-----KPRKILDLGCGIGGSSLYLAQQHQAEVMGASLSPVQVERA
SEQ ID NO:40   RMIEESLRFAGVTDEEE-EKKIKKVVDVGCGIGGSSRYLASKFGAECIGITLSPVQAKRA
SEQ ID NO:38   RMIEEALAFAAVP--DDPTNKPKTIVDVGCGIGGSSRYLANKYGAQCSGITLSPVQAERG
SEQ ID NO:28   RMIQESLRFASV--SEERSKWPKSIVDVGCGIGGSSRYLAKKFGATSVGITLSPVQAQRA
SEQ ID NO:08   RMIQESLRFASV--SEERSKWPKSIVDVGCGIGGSSRYLAKKFGATSVGITLSPVQAQRA
SEQ ID NO:22   RMIEEALAFAGVPASDDPEKTPKTIVDVGCGIGGSSRYLAKKYGXQCTGITLSPVQAERG
SEQ ID NO:24   RMIEESLAFA------------------------------------------------
SEQ ID NO:26   ----------------------------------------------------------
                121                                                            180
```

FIGURE 1B

```
SEQ ID NO:39    GERARALGLGSTCQFQVANALDLPFASDSFDWVSLESGEHMPNKAQFLQEAWRVLKPGG
SEQ ID NO:40    NDLAAAQSLSHKASFQVADALDQPFEDGKFDLVWSMESGEHMPDKAKFVKELVRVAAPGG
SEQ ID NO:38    NALAAAQGLSDKASFQVADALEQPFPDGQFDLVWSMESGEHMPNKQKFVSELARVAAPGA
SEQ ID NO:28    NALAAAQGLADKVSFQVADALQQPFSDGQFDLVWSMESGEHMPDKAKFVGELARVAAPGA
SEQ ID NO:08    NALAAAQGLADKVSFQVADALQQPFSDGQFDLVWSMESGEHMPDKAKFVGELARVAAPGA
SEQ ID NO:22    NALAAAQGLSDQVTLQVADALEQPFPDGQFDLVWSMESGEHMPDKRKFVSELARVAAPGG
SEQ ID NO:24    ------------------------------------------------------------
SEQ ID NO:26    ---------------AQPFPDGQFDLVWSMESDEHMPDKRQFVSELARVAAPGA
                                                                          240

SEQ ID NO:39    RLILATWCHRPIDPGNGPLTADERRHLQAIYDVYCLPYVVSLPDYEAIARECGFGEIKTA
SEQ ID NO:40    RIIIVTWCHRNLSAGEEALQPWEQNILDKICKTFYLPAWCSTDDYVNLLQSHSLQDIKCA
SEQ ID NO:38    TIIIVTWCHRNLAPSEDSLKPDELNLLKKICDAYYLPDWCSPSDYVKIAESLSLEDIKTA
SEQ ID NO:28    IIIIVTWCHRDLGPDEQSLHPWEQDLLKKICDAYYLPAWCSTSDYVKLLQSLSLQDIKSE
SEQ ID NO:08    IIIIVTWCHRDLGPDEQSLHPWEQDLLKKICDAYYLPAWCSTSDYVKLLQSLSLQDIKSE
SEQ ID NO:22    TIIIVTWCHRNLDPSETSLKPDELSLLRRICDAYYLPDWCSPSDYVNIAKSLSLEDIKTA
SEQ ID NO:24    ------------------------------------------------------------
SEQ ID NO:26    RIIIVTWCHRNLEPSEESLKPDELNLLKRICDAYYLPDWCSPSDYVKIAESLSLEDIRTA
                                                                          300

SEQ ID NO:39    DWSVAVAPFWDRVIESAFDPRVLWALGQAGPKIINAALCLRLMKWGYERGLVRFGLLTGI
SEQ ID NO:40    DWSENVAPFWPAVIRTALTWKGLVSLLRSGMKSIKGALTMPLMIEGYKKGVIKFGIITCQ
SEQ ID NO:38    DWSENVAPFWPAVIQSALTWKGLTSLLRSGWKTIKGALVMPLMIQGYKKGLIKFSIITCR
SEQ ID NO:28    DWSRFVAPFWPAVIRSAFTWKGLSSLLSSGQKTIKGALAMPLMIEGYKKDLIKFAIITCR
SEQ ID NO:08    DWSRFVAPFWPAVIRSAFTWKGLSSLLSSGKLGI------YIAFQKQTPPSSIATCK
SEQ ID NO:22    DWSENVAPFWPAVIKSALTWKGFTSLLTTGWKTIRGAMVMPLMIQGYKKGLIKFTIITCR
SEQ ID NO:24    ------------------------------------------------------------
SEQ ID NO:26    DWSENVAPFWPAVIKSALTWKGLTSLLRSGWETVRGAMVMPLVIEGYKKGLIKFPIITCR
                                                                          360
```

FIGURE 1C

```
SEQ ID NO:39    KPLV----------------------
SEQ ID NO:40    KPL-----------------------
SEQ ID NO:38    KPQAAIEGEPEAASPSVE.-------
SEQ ID NO:28    K------PE.----------------
SEQ ID NO:08    SYVTDHYFHTR.--------------
SEQ ID NO:22    KPGAA-.MA----HAALLHC------
SEQ ID NO:24    --------------------------
SEQ ID NO:26    KPETT----------Q.-
                361                      380
```

FIGURE 2A

```
SEQ ID NO:41      MPPTPTTPAATGAAAAVTPEHARPH-----RMVRFNPRSDRFHTLSFHHVEFWCADAASA
SEQ ID NO:43      MGHQNAAVSENQNHDDGAASSPGFKLVGFSKFVRKNPKSDKFKVKRFHHIEFWCGDATNV
SEQ ID NO:42      MGKKQSEAEILSS-NSSNTSPATFKLVGFNNFVRANPKSDHFAVKRFHHIEFWCGDATNT
SEQ ID NO:36      MPIPMCNEIQAQA-QAQAQAQPGFKLVGFKNFVRTNPKSDRFQVNRFHHIEFWCTDATNA
SEQ ID NO:38      MPPTPTTPAATGAAAA-VTPEHARPR-----RMVRFNPRSDRFHTLAFHHVEFWCADAASA
SEQ ID NO:32      MGK-QTTTSATAA-DGSKDAHAEFKLVGFKNFVRTNPKSDHFCVHRFHHIEFWCGDATNT
                  1                                                          60

SEQ ID NO:41      AGRFAFALGAPLAARSDLSTGNSAHASQLLRSGSLAFLFTAPYANG------CDAATASL
SEQ ID NO:43      ARRFSWGLGMRFSAKSDLSTGNMVHASYLLTSGDLRFLFTAPYSPSLSAGEIKPTTTASI
SEQ ID NO:42      SRRFSWGLGMPLVAKSDLSTGNSVHASYLVRSANLSFVFTAPYSPSTTTSS-G---SAAI
SEQ ID NO:36      SRRFSWGLGMPIVAKSDLSTGNQIHASYLLRSGDLSFLFSAPYSPSLSAGS-SAASSASI
SEQ ID NO:38      AGRFAFALGAPLAARSDLSTGNSVHASQLLRSGNLAFLFTAPYANG------CDAATASL
SEQ ID NO:32      AKRFSWGLGMPLVAKSDLSTGNSAHASYLLRSGELNFLFTSPYSPSISAPS-----SAAI
                  61                                                         120

SEQ ID NO:41      PSFSADAARRFSADHGIAVRSVALRVADAAEEAFRASRRRGARPAFAPVDLGRGFA-FAEV
SEQ ID NO:43      PSFDHGSCRSFSFFSSHGLGVRVAVAIEVEDAESAFSISVANGAIPSSPPIVLNEAVT-IAEV
SEQ ID NO:42      PSFSASGFHSFAAKHGLAVRAIALEVADVAAAFEASVARGARPASAPVEL-DDQAWLAEV
SEQ ID NO:36      PSFDAATCLAFAAKHGFGVRAIALEVADAEAAFSASVAKGAEPASPPV-LVDDRTGFAEV
SEQ ID NO:38      PSFSADAARQFSADHGLAVRSIALRVADAAEEAFRASVDGGARPAFSPVDLGRGFG-FAEV
SEQ ID NO:32      PSFSFSTYQSFTSSHGLAVRAVAIQVDSAFSAYSASISRGAKPVSAPILLSDNKTAIAEV
                  121                                                        180
```

FIGURE 2B

```
SEQ ID NO:41   ELYGDVVLRFVSH-PDGTDVP------FLPGFEGVTNPDA---VDYGLTRFDHVVGNVP
SEQ ID NO:43   KLYGDVVLRYVSYKAEDTEKSE-----FLPGFERVEDASSFP-LDYGIRRLDHAVGNVP
SEQ ID NO:42   ELYGDVVLRFVSFGRE-------EGLFLPGFEAVEGTASFPDLDYGIRRLDHAVGNVT
SEQ ID NO:36   RLYGDVVLRYVSYKDAAPQAPHADPSRWFLPGFEAAASSSSFPELDYGIRRLDHAVGNVP
SEQ ID NO:38   ELYGDVVLRFVSH-PDGRDVP------FLPGFEGVSNPDA---VDYGLTRFDHVVGNVP
SEQ ID NO:32   HLYGDSVLRFVSYGDNG------TGPDGWFLPGFEPVDDQMSYKELDYGIRRLDHAVGNVP
                                                                          240
               181

SEQ ID NO:41   ELAPAAAYIAGFTGFHEFAEFTAEDVGTTESGLNSVVLANNSEGVLLPLNEPVHGTKRRS
SEQ ID NO:43   ELGPALTYVAGFTGFHQFAEFTADDVGTAESGLNSAVLASNDEMVLLPINEPVHGTKRKS
SEQ ID NO:42   ELGPVVEYIKGFTGFHEFAEFTAEDVGTLESGLNSVVLANNEEMVLLPLNEPVYGTKRKS
SEQ ID NO:36   ELAPAVRYLKGFSGFHEFAEFTAEDVGTSESGLNSVVLANNSETVLLPLNEPVYGTKRKS
SEQ ID NO:38   ELAPAAAYVAGFTGFHEFAEFTTEDVGTAESGLNSMVLANNSEGVLLPLNEPVHGTKRRS
SEQ ID NO:32   ELGPVVDYLKKFTGFHEFAEFTSEDVGTAESGLNSMVLANNNENVLLPLNEPVFGTKRKS
                                                                          300
               241

SEQ ID NO:41   QIQTFLEHHGGPGVQHIAVASSDVLRTLRKMRARSAMGGFDFLPPPLPKYYEGVRRLAGD
SEQ ID NO:43   QIQTYLEHNEGAGLQHLALMSEDIFRTLREMRKRSSIGGFDFMPSPPPTYYQNLKKRVGD
SEQ ID NO:42   QIQTYLEHNEGAGVQHLALVSEDIFRTLREMRKRSCLGGFEFMPSPPPTYYKNLKNRVGD
SEQ ID NO:36   QIETYLEHNEGAGVQHLALVTHDIFTTLREMRKRSFLGGFEFMPSPPPTYYANLHNRAAD
SEQ ID NO:38   QIQTFLEHHGGSSVQHIAVASSDVLRTLREMRARSAMGGFDFLPPPLPKYYEGVRRIAGD
SEQ ID NO:32   QIQTYLEHNEGPGVQHLALVSEDIFNTLREMRKRSGVGGFEFMPSPPLTYYKNLKNRAGD
                                                                          360
               301
```

FIGURE 2C

```
SEQ ID NO:41    VLSEAQIKECQELGVLVDRDDQGVLLQIFTKPVGDRPTLFLEMIQRIGCMEKDERGEEYQ
SEQ ID NO:43    VLSDDQIKECEELGILVDRDDQGTLLQIFTKPLGDRPTIFIEIIQRVGCMMKDEEGKAYQ
SEQ ID NO:42    VLSDEQIKECEDLGILVDRDDQGTLLQIFTKPVGDRPTLFIEIIQRVGCMLKDDAGQMYQ
SEQ ID NO:36    VLTVDQIKQCEELGILVDRDDQGTLLQIFTKPVGDRPTIFIEIIQRIGCMVEDEEGKVYQ
SEQ ID NO:38    VLSEAQIKECQELGVLVDRDDQGVLLQIFTKPVGDRPTLFLEMIQRIGCMEKDERGEEYQ
SEQ ID NO:32    VLRDEQIEECEKLGILVDRDDQGTLLQIFTKPVGDRPTLFIEIIQRIGCMLKDEQGKLYQ
                361                                                      420

SEQ ID NO:41    KGGCGGFGKGNFSELFKSIEDYEKSLEAKQSAAVQG-S
SEQ ID NO:43    SGGCGGFGKGNFSELFKSIEEYEKTLEAKQLVG-----
SEQ ID NO:42    KGGCGGFGKGNFSELFKSIEEYEKTLEAKQITGSA-AA
SEQ ID NO:36    KGACGGFGKGNFSELFKSIEEYEKTLEAKR-----TA.
SEQ ID NO:38    KGGCGGFGKGNFSELFKSIEDYEKSLEAKQSAAVQGS.
SEQ ID NO:32    KSGCGGFGKGNFSELFKSIEEYEKMLEAKQVTETASA.
                421                              458
```

PLANT VITAMIN E BIOSYNTHETIC ENZYMES

This application is a divisional of U.S. application Ser. No. 09/857,613, filed Jun. 4, 2001 now U.S. Pat. No. 7,071,381, allowed, which is a National Stage Application of PCT/US99/28588, filed Dec. 2, 1999, which claims the benefit of U.S. Provisional Application No. 60/110,781, filed Dec. 3, 1998, each of which references is hereby incorporated by reference in its entirety.

FIELD OF THE INVENTION

This invention is in the field of plant molecular biology. More specifically, this invention pertains to nucleic acid fragments encoding vitamin E biosynthetic enzymes in plants and seeds.

BACKGROUND OF THE INVENTION

Vitamin E (alpha-tocopherol) is an essential element in the mammalian diet since mammals can not synthesize plastoquinones or tocopherols. The first step in the formation of plastoquinones and tocopherols in plants is the formation of homogenistate from 4-hydroxyphenylpyruvate, a reaction catalyzed by 4-hydroxyphenylpyruvate dioxygenase (EC 1.13.11.27). Genetic mutants of this enzyme in *Arabidopsis* are deficient in both carotenoids and tocopherols (Norris et al. (1995) *Plant Cell* 7:2139–2149). Carotenoids (xanthopylls) in corn endosperm are valuable coloring agents in poultry feeds; tocopherols are antioxidants which may be important in oil stability and human health. Generally present at low levels in plant tissues, 4-hydroxyphenylpyruvate dioxygenase catalyzes a complex, irreversible reaction. Only recently has 4-hydroxyphenylpyruvate dioxygenase been purified to homogeneity from a plant source (Garcia et al. (1997 *Biochem. J.* 325:761–769). In plants, cDNAs encoding 4-hydroxyphenylpyruvate dioxygenase have been identified in carrots, barley and *Arabidopsis thaliana* with at least two different variants existing in this last plant. 4-Hydroxyphenylpyruvate dioxygenase is a known herbicide target (Mayonado et al. (1989) *Pestic. Biochem. Physiol.* 35:138–145; Schultz et al. (1993) *FEBS lett.* 318:162–166; Secor (1994) *Plant Phys.* 106:1429–1433). Even though plastoquinones and tocopherols are not synthesized by mammals and bacteria 4-hydroxyphenylpyruvate dioxygenase activity is present, often at high levels, and involved in phenylalanine and tyrosine degradation. Among others, the cDNAs encoding 4-hydroxyphenylpyruvate dioxygenase have been identified in *Mycosphaerella graminicola*, mice and *Coccidiodes immitis*.

Plants synthesize alpha, beta, gamma and delta tocopherols of which alpha tocopherol (vitamin E) has the highest value for human nutrition. In soybean 7% of the tocopherols are vitamin E. Gamma tocopherol methyltransferase catalyzes the final step in vitamin E synthesis and has been purified to homogeneity from pepper, marigold, *Euglena* and spinach. The gene encoding gamma tocopherol methyltransferase from *Synechocystis* was identified by mutating an open reading frame encoding a methyltransferase located in the operon containing the 4-hydroxyphenylpyruvate dioxygenase gene in the *Synechocystis* genomic sequence (Shintani and Della Penna (1998) Abstract for the American Society of Plant Physiologists meeting in Madison, Wis.).

Since mammals can not synthesize tocopherols, the enzymes described here may be used for the discovery of new herbicides.

SUMMARY OF THE INVENTION

The present invention relates to isolated polynucleotides comprising a nucleotide sequence encoding a polypeptide of at least 160 amino acids that has at least 80% identity based on the Clustal method of alignment when compared to a polypeptide selected from the group consisting of a corn gamma-tocopherol methyltransferase polypeptide of SEQ ID NOs:2 and 22, a rice gamma-tocopherol methyltransferase polypeptide of SEQ ID NOs:4, 6, 24, and 26, a soybean gamma-tocopherol methyltransferase polypeptide of SEQ ID NOs:8 and 28, and a wheat gamma-tocopherol methyltransferase polypeptide of SEQ ID NOs:10 and 30. The present invention also relates to an isolated polynucleotide comprising the complement of the nucleotide sequences described above.

The present invention relates to isolated polynucleotides comprising a nucleotide sequence encoding a polypeptide of at least 150 amino acids that has at least 95% identity based on the Clustal method of alignment when compared to a polypeptide selected from the group consisting of a catalpa 4-hydroxyphenylpyruvate dioxygenase polypeptide of SEQ ID NO:32, a rice 4-hydroxyphenylpyruvate dioxygenase polypeptide of SEQ ID NOs: 12, 14, and 34, a soybean 4-hydroxyphenylpyruvate dioxygenase polypeptide of SEQ ID NOs: 16 and 36, a Vernonia 4-hydroxyphenylpyruvate dioxygenase of SEQ ID NO: 18, and a wheat 4-hydroxyphenylpyruvate dioxygenase polypeptide of SEQ ID NOs:20 and 38. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs: 1, 3, 5, 7, 9, 11, 13, 15, 17, 19, 21, 23, 25, 27, 29, 31, 33, 35, and 37 that codes for the polypeptide selected from the group consisting of SEQ ID NOs:2, 4, 6, 8, 10, 12, 14, 16, 18, 20, 22, 24, 26, 28, 30, 32, 34, 36, and 38. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a gamma-tocopherol methyltransferase polypeptide of at least 160 amino acids comprising at least 80% homology based on the Clustal method of alignment compared to a polypeptide selected from the group consisting of SEQ ID NOs:2, 4, 6, 8, 10, 22, 24, 26, 28, and 30.

The present invention relates to a 4-hydroxyphenylpyruvate dioxygenase polypeptide of at least 150 amino acids comprising at least 95% homology based on the Clustal method of alignment compared to a polypeptide selected from the group consisting of SEQ ID NOs: 12, 14, 16, 18, 20, 32, 34, 36, and 38.

The present invention relates to a method of selecting an isolated polynucleotide that affects the level of expression of a gamma-tocopherol methyltransferase or a 4-hydroxy-phenylpyruvate dioxygenase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a gamma-tocopherol methyltransferase or a 4-hydroxyphenylpyruvate dioxygenase polypeptide in the host cell containing the isolated polynucleotide; and (d) comparing the level of a gamma-tocopherol methyltransferase or a 4-hydroxyphenylpyruvate dioxygenase polypeptide in the host cell containing the isolated polynucleotide with the level of a gamma-tocopherol methyltransferase or a 4-hydroxyphenylpyruvate dioxygenase polypeptide in the host cell that does not contain the isolated polynucleotide.

The present invention relates to a method of obtaining a nucleic acid fragment encoding a substantial portion of a gamma-tocopherol methyltransferase or a 4-hydroxyphenylpyruvate dioxygenase polypeptide gene, preferably a plant gamma-tocopherol methyltransferase or 4-hydroxyphenylpyruvate dioxygenase polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, and the complement of such nucleotide sequences; and amplifying a nucleic acid fragment (preferably a cDNA inserted in a cloning vector) using the oligonucleotide primer. The amplified nucleic acid fragment preferably will encode a portion of a gamma-tocopherol methyltransferase or a 4-hydroxyphenylpyruvate dioxygenase amino acid sequence.

The present invention also relates to a method of obtaining a nucleic acid fragment encoding all or a substantial portion of the amino acid sequence encoding a 4-hydroxyphenylpyruvate dioxygenase or a gamma tocopherol methyltransferase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a 4-hydroxyphenylpyruvate dioxygenase or a gamma tocopherol methyltransferase, the method comprising the steps of: (a) transforming a host cell with a chimeric gene comprising a nucleic acid fragment encoding a 4-hydroxyphenylpyruvate dioxygenase or a gamma tocopherol methyltransferase, operably linked to suitable regulatory sequences; (b) growing the transformed host cell under conditions that are suitable for expression of the chimeric gene wherein expression of the chimeric gene results in production of 4-hydroxyphenylpyruvate dioxygenase or gamma tocopherol methyltransferase in the transformed host cell; (c) optionally purifying the 4-hydroxyphenylpyruvate dioxygenase or the gamma tocopherol methyltransferase expressed by the transformed host cell; (d) treating the 4-hydroxyphenylpyruvate dioxygenase or the gamma tocopherol methyltransferase with a compound to be tested; and (e) comparing the activity of the 4-hydroxyphenylpyruvate dioxygenase or the gamma tocopherol methyltransferase that has been treated with a test compound to the activity of an untreated 4-hydroxyphenylpyruvate dioxygenase or gamma tocopherol methyltransferase, thereby selecting compounds with potential for inhibitory activity.

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, 11, 13, 15, 17, 19, 21, 23, 25, 27, 29, 31, 33, 35, and 37.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the gamma-tocopherol methyltransferase or a 4-hydroxyphenylpyruvate dioxygenase polynucleotide in an amount sufficient to complement a null mutant to provide a positive selection means.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A–1C show a comparison of the amino acid sequences of the gamma-tocopherol methyltransferase from soybean contig assembled from clones sah1c.pk001.k8, sgc5c.pk001.m23, and sah1c.pk004.g2 (SEQ ID NO:8), corn contig assembled from clones cr1n.pk0179.f10:fis, cs1.pk0065.f2, cta1n.pk0031.d2, p0060.coran49r, and p0103.ciaay86r (SEQ ID NO:22, the 3'-end sequence of rice clone rls72.pk0010.g3 (SEQ ID NO:24), the 5'-end sequence of clone rls72.pk0010.g3 (SEQ ID NO:26), soybean clone sah1c.pk004.g2 (SEQ ID NO:28), wheat clone wr1.pk0077.f1:fis (SEQ ID NO:30), *Synechocystis* sp. (NCBI General Identifier No. 1001725; SEQ ID NO:39), and *Arabidopsis thaliana* (NCBI General Identifier No. 4106538; SEQ ID NO:40). Dashes are used by the program to maximize the alignment.

FIGS. 2A–2C show a comparison of the amino acid sequences of the 4-hydroxyphenyl-pyruvate dioxygenase from catalpa clone ncs.pk0012.g1:fis (SEQ ID NO:32), soybean clone sgc5c.pk001.j9:fis (SEQ ID NO:36), wheat clone wdk4c.pk006.m9:fis (SEQ ID NO:38), *Hordeum vulgare* having NCBI General Identifier No. 3334222 (SEQ ID NO:41), *Daucus carota* having NCBI General Identifier No. 3334219 (SEQ ID NO:42), and *Arabidopsis thaliana* having NCBI General Identifier No. 3334223 (SEQ ID NO:43). Dashes are used by the program to maximize the alignment.

FIG. 3 depicts the distribution of the percent of alpha- and gamma-tocopherol content of 25 transgenic soybean lines transformed with the gamma tocopherol methyltransferase sequence from clone sah1c.pk001.k8.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Vitamin E Biosynthetic Enzymes

| Protein | Clone Designation | SEQ ID NO: (Nucleotide) | SEQ ID NO: (Amino Acid) |
| --- | --- | --- | --- |
| Corn Gamma Tocopherol Methyltransferase | Contig of: cr1n.pk0179.f10 cs1.pk0065.e1 cs1.pk0065.f2 cta1n.pk0031.d2 | 1 | 2 |
| Rice Gamma Tocopherol Methyltransferase | rl0n.pk085.e11 | 3 | 4 |
| Rice Gamma Tocopherol Methyltransferase | Contig of: rl0n.pk099.d24 rls72.pk0010.g3 | 5 | 6 |
| Soybean Gamma Tocopherol Methyltransferase | Contig of: sah1c.pk001.k8 sgc5c.pk001.m23 sah1c.pk004.g2 | 7 | 8 |
| Wheat Gamma Tocopherol Methyltransferase | Contig of: wr1.pk0077.f1 wr1.pkl77.b11 wle1n.pk0065.h9 wre1n.pk0111.d6 | 9 | 10 |
| Rice 4-Hydroxyphenyl-pyruvate Dioxygenase | rlr12.pk0019.g5 | 11 | 12 |
| Rice 4-Hydroxyphenyl-pyruvate Dioxygenase | rlr12.pk0025.e4 | 13 | 14 |
| Soybean 4-Hydroxyphenyl-pyruvate Dioxygenase | Contig of: sgc5c.pk001.j9 sgs1c.pk002.a8 sfl1.pk126.n15 sgs1c.pk003.o5 sgc4c.pk001.p2 | 15 | 16 |
| *Vernonia* 4-Hydroxyphenyl-pyruvate Dioxygenase | vs1.pk0015.b2 | 17 | 18 |
| Wheat 4-Hydroxyphenyl-pyruvate Dioxygenase | Contig of: wdk4c.pk006.m9 wlmk1.pk0021.h10 wlmk1.pk0019.e2 wlm0.pk0035.d5 wlmk1.pk0013.g11 | 19 | 20 |
| Corn Gamma Tocopherol Methyltransferase | Contig of: cr1n.pk0179.f10:fis cs1.pk0065.f2 cta1n.pk0031.d2 p0060.coran49r p0103.ciaay86r | 21 | 22 |
| Rice Gamma Tocopherol Methyltransferase | rls72.pk0010.g3-3' | 23 | 24 |
| Rice Gamma Tocopherol Methyltransferase | rls72.pk0010.g3-5' | 25 | 26 |
| Soybean Gamma Tocopherol Methyltransferase | sah1c.pk004.g2 | 27 | 28 |
| Wheat Gamma Tocopherol Methyltransferase | wr1.pk0077.f1:fis | 29 | 30 |
| *Catalpa* 4-Hydroxyphenyl-pyruvate Dioxygenase | ncs.pk0012.g1:fis | 31 | 32 |
| Rice 4-Hydroxyphenyl-pyruvate Dioxygenase | rlr12.pk0025.e4:fis | 33 | 34 |
| Soybean 4-Hydroxyphenyl-pyruvate Dioxygenase | sgc5c.pk001.j9:fis | 35 | 36 |
| Wheat 4-Hydroxyphenyl-pyruvate Dioxygenase | wdk4c.pk006.m9:fis | 37 | 38 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, 25, 27, 29, 31, 33, 35, 37, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37 and the complement of such nucleotide sequences may be used in methods of selecting an isolated polynucleotide that affects the expression of a polypeptide (vitamin E biosynthetic enzyme) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3'non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several vitamin E biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other 4-hydroxyphenylpyruvate dioxygenases or gamma tocopherol methyltransferases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as gamma tocopherol methyltransferase or 4-phenylpyruvate dioxygenase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (gamma tocopherol methyltransferase or 4-phenylpyruvate dioxygenase).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of homogenistate in those cells. Overexpression of 4-hydroxyphenylpyruvate dioxygenase should result in a larger accumulation of homogenistate which may be used by gamma tocopherol methyltransferase to produce vitamin E. Since mammals can not synthesize tocopherols, the enzymes described herein may be used for the discovery of new herbicides.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded vitamin E biosynthetic enzyme. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze various steps in vitamin E biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries, Isolation and Sequencing of cDNA Clones cDNA libraries representing mRNAs from various corn, rice, soybean, *Vernonia*, and wheat tissues were prepared. The characteristics of the libraries are described below.

TABLE 2 cDNA Libraries from cDNA Libraries from Corn, Rice, Soybean, *Vernonia*, and Wheat

| Library | Tissue | Clone |
|---|---|---|
| cr1n | Corn Root From 7 Day Old Seedlings* | cr1n.pk0155.d1 |
| cr1n | Corn Root From 7 Day Old Seedlings* | cr1n.pk0179.f10 |
| cs1 | Corn Leaf Sheath From 5 Week Old Plant | cs1.pk0065.e1 |
| cs1 | Corn Leaf Sheath From 5 Week Old Plant | cs1.pk0065.f2 |
| cta1n | Corn Tassel* | cta1n.pk0031.d2 |
| ncs | *Catalpa speciosa* Developing Seed | ncs.pk0012.g1 |
| p0023 | Corn Leaf From Plant Transformed with Gene M1C07 (leucine-rich repeat) Which Induces Resistance Prior to Genetic Lesion Formation. Harvested About One Month After Planting in Green House* | p0060.coran49r |
| p0103 | Corn Tassel Shoots(0.1–1.4 cm)* | p0103.ciaay86r |
| rl0n | Rice 15 Day Old Leaf* | rl0n.pk085.e11 |
| rl0n | Rice 15 Day Old Leaf* | rl0n.pk099.d24 |
| rlr12 | Rice Leaf 15 Days After Germination, 12 Hours After Infection of Strain *Magaporthe grisea* 4360-R-62 (AVR2-YAMO); Resistant | rlr12.pk0019.g5 |
| rlr12 | Rice Leaf 15 Days After Germination, 12 Hours After Infection of Strain *Magaporthe grisea* 4360-R-62 (AVR2-YAMO); Resistant | rlr12.pk0025.e4 |
| rls72 | Rice Leaf 15 Days After Germination, 72 Hours After Infection of Strain *Magaporthe grisea* 4360-R-67 (AVR2-YAMO); Susceptible | rls72.pk0010.g3 |
| sah1c | Soybean Sprayed With Authority Herbicide | sah1c.pk001.k8 |
| sah1c | Soybean Sprayed With Authority Herbicide | sah1c.pk004.g2 |
| sfl1 | Soybean Immature Flower | sfl1.pk126.n15 |
| sgc4c | Soybean Cotyledon 14–21 Days After Germination (¼ yellow) | sgc4c.pk001.p2 |
| sgc5c | Soybean (Cotyledon 15–24 Days After Germination (¾ yellow) | sgc5c.pk001.j9 |
| sgc5c | Soybean (Cotyledon 15–24 Days After Germination (¾ yellow) | sgc5c.pk001.m23 |
| sgs1c | Soybean Seeds 4 Hours After Germination | sgs1c.pk002.a8 |
| sgs1c | Soybean Seeds 4 Hours After Germination | sgs1c.pk003.o5 |
| vs1 | *Vernonia* Seed Stage 1 | vs1.pk0015.b2 |
| wdk4c | Wheat Developing Kernel, 21 Days After Anthesis | wdk4c.pk006.m9 |
| wle1n | Wheat Leaf From 7 Day Old Etiolated Seedling* | wle1n.pk0065.h9 |
| wlm0 | Wheat Seedlings 0 Hour After Inoculation With *Erysiphe graminis* f. sp *tritici* | wlm0.pk0035.d5 |
| wlmk1 | Wheat Seedlings 1 Hour After Inoculation With *Erysiphe graminis* f. sp *tritici* and Treatment With Herbicide** | wlmk1.pk0013.g11 |
| wlmk1 | Wheat Seedlings 1 Hour After Inoculation With *Erysiphe graminis* f. sp *tritici* and Treatment With Herbicide** | wlmk1.pk0019.e2 |
| wlmk1 | Wheat Seedlings 1 Hour After Inoculation With *Erysiphe graminis* f. sp *tritici* and Treatment With Herbicide** | wlmk1.pk0021.h10 |
| wr1 | Wheat Root From 7 Day Old Seedling | wr1.pk0077.f1 |
| wr1 | Wheat Root From 7 Day Old Seedling | wr1.pk177.b11 |
| wre1n | Wheat Root From 7 Day Old Etiolated Seedling* | wre1n.pk0111.d6 |

*These libraries were normalized essentially as described in U.S. Pat. No. 5,482,845, incorporated herein by reference.
**Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding vitamin E biosynthetic enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Gamma Tocopherol Methyltransferase

The BLASTX search using the EST sequences from clones listed in Table 3 revealed similarity of the polypeptides encoded by the cDNAs to gamma tocopherol methyltransferase from *Synechocystis* sp. (NCBI General Identifier No. 1001725). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to gamma Tocopherol Methyltransferase

| Clone | Status | BLAST pLog Score 1001725 |
|---|---|---|
| Contig of: | Contig | 49.70 |
| cr1n.pk0179.f10 | | |
| cs1.pk0065.e1 | | |
| cs1.pk0065.f2 | | |
| cta1n.pk0031.d2 | | |
| r10n.pk085.e11 | EST | 15.10 |
| Contig of: | Contig | 8.30 |
| r10n.pk099.d24 | | |
| rls72.pk0010.g3 | | |
| Contig of: | CGS | 64.22 |
| sah1c.pk001.k8 | | |
| sgc5c.pk001.m23 | | |
| sah1c.pk004.g2:fis | | |

TABLE 3-continued

BLAST Results for Sequences Encoding Polypeptides Homologous to gamma Tocopherol Methyltransferase

| Clone | Status | BLAST pLog Score 1001725 |
|---|---|---|
| Contig of: | Contig | 57.00 |
| wr1.pk0077.f1 | | |
| wr1.pk177.b11 | | |
| wle1n.pk0065.h9 | | |
| wre1n.pk0111.d6 | | |

Further sequencing and searching of the DuPont proprietary database allowed for the assembly of longer sequences. The BLASTX search using the nucleotide sequences from clones listed in Table 4 revealed similarity of the polypeptides encoded by the cDNAs to gamma tocopherol methyltransferase from *Arabidopsis thaliana* (NCBI General Identifier No. 4106538). Shown in Table 4 are the BLAST results for individual ESTs ("EST") or sequences encoding the entire protein derived from the sequences of the entire cDNA inserts comprising the indicated cDNA clones ("FIS"), contigs assembled from an FIS and one or more ESTs, or an FIS and PCR ("CGS"):

TABLE 4

BLAST Results for Sequences Encoding Polypeptides Homologous to gamma Tocopherol Methyltransferase

| Clone | Status | BLAST pLog Score 4106538 |
|---|---|---|
| Contig of: | CGS | 118.00 |
| cr1n.pk0179.f10:fis | | |
| cs1.pk0065.f2 | | |
| cta1n.pk0031.d2 | | |
| p0060.coran49r | | |
| p0103.ciaay86r | | |
| rls72.pk0010.g3-3' | EST* | 81.30 |
| rls72.pk0010.g3-5' | EST* | 11.00 |
| sah1c.pk004.g2 | CGS | 125.00 |
| wr1.pk0077.f1:fis | CGS | 120.00 |

*These sequences are derived from partial full-insert sequencing of clone rls72.pk0010.g3 and correspond to 5'-end and 3'-end sequences.

FIGS. 1A–1C present an alignment of the amino acid sequences set forth in SEQ ID NOs:8, 22, 24, 26, 28, and 30 and the *Synechocystis* sp. and *Arabidopsis thaliana* sequences (SEQ ID NO:39 and SEQ ID NO:40, respectively). The data in Table 5 represents a calculation of the percent identity of the amino acid sequences set forth in SEQ ID NOs:8, 22, 24, 26, 28, and 30 and the *Synechocystis* sp. and *Arabidopsis thaliana* sequences (SEQ ID NO:39 and SEQ ID NO:40, respectively).

TABLE 5

Percent Identity of Amino Acid Sequences Deduced From the Nucleotide Sequences of cDNA Clones Encoding Polypeptides Homologous to gamma Tocopherol Methyltransferase

| | Percent Identity to | |
|---|---|---|
| SEQ ID NO. | 1001725 | 4106538 |
| 8 | 37.9 | 56.9 |
| 22 | 42.6 | 58.6 |
| 24 | 42.8 | 67.6 |
| 26 | 23.8 | 33.3 |

TABLE 5-continued

Percent Identity of Amino Acid Sequences Deduced From the
Nucleotide Sequences of cDNA Clones Encoding Polypeptides
Homologous to gamma Tocopherol Methyltransferase

| | Percent Identity to | |
|---|---|---|
| SEQ ID NO. | 1001725 | 4106538 |
| 28 | 41.3 | 62.6 |
| 30 | 43.2 | 59.5 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode one entire corn, two entire soybean, one entire wheat, and two fragments corresponding to an almost entire ricce gamma tocopherol methyltransferase. These sequences represent the first corn, rice, soybean, and wheat sequences encoding gamma tocopherol methyltransferase.

Example 4

Characterization of cDNA Clones Encoding 4-Hydroxyphenylpyruvate Dioxygenase

The BLASTX search using the EST sequences from clones listed in Table 6 revealed similarity of the polypeptides encoded by the cDNAs to 4-hydroxyphenylpyruvate dioxygenase from *Hordeum vulgare* (NCBI General Identifier No. 3334222), *Daucus carota* (NCBI General Identifier No. 3334219) and *Arabidopsis thaliana* (NCBI General Identifier No. 3334223). Shown in Table 6 are the BLAST results for individual ESTs ("EST") or contigs assembled from two or more ESTs ("Contig"):

TABLE 6

BLAST Results for Sequences Encoding Polypeptides
Homologous to 4-Hydroxyphenylpyruvate Dioxygenase

| | | BLAST pLog Score | | |
|---|---|---|---|---|
| Clone | Status | 3334222 | 3334219 | 3334223 |
| rlr12.pk0019.g5 | EST | 26.70 | 17.70 | 18.00 |
| rlr12.pk0025.e4 | EST | 58.52 | 50.40 | 49.40 |
| Contig of: sgc5c.pk001.j9 sgs1c.pk002.a8 sfl1.pk126.n15 sgs1c.pk003.o5 sgc4c.pk001.p2 | Contig | 55.00 | 81.30 | 107.00 |
| vs1.pk0015.b2 | EST | 39.40 | 51.70 | 52.05 |
| Contig of: wdk4c.pk006.m9 wlmk1.pk0021.h10 wlmk1.pk0019.e2 | Contig | 176.00 | 102.00 | 97.00 |

TABLE 6-continued

BLAST Results for Sequences Encoding Polypeptides
Homologous to 4-Hydroxyphenylpyruvate Dioxygenase

| | | BLAST pLog Score | | |
|---|---|---|---|---|
| Clone | Status | 3334222 | 3334219 | 3334223 |
| wlm0.pk0035.d5 wlmk1.pk0013.g11 | | | | |

Further sequencing and searching of the DuPont proprietary database allowed the assembly of longer sequences and identification of 4-hydroxyphenylpyruvate dioxygenase in other species. The BLASTX search using the nucleotide sequences from clones listed in Table 7 revealed similarity of the polypeptides encoded by the cDNAs to 4-hydroxyphenyl-pyruvate dioxygenase from *Hordeum vulgare* (NCBI General Identifier No. 3334222), *Daucus carota* (NCBI General Identifier No. 3334219) and *Arabidopsis thaliana* (NCBI General Identifier No. 3334223). Shown in Table 7 are the BLAST results for the sequences of the entire cDNA inserts comprising the indicated cDNA clones ("FIS") or sequences encoding the entire protein derived from an FIS, or an FIS and PCR ("CGS"):

TABLE 7

BLAST Results for Sequences Encoding Polypeptides
Homologous to 4-Hydroxyphenylpyruvate Dioxygenase

| | | BLAST pLog Score | | |
|---|---|---|---|---|
| Clone | Status | 3334222 | 3334219 | 3334223 |
| ncs.pk0012.g1:fis | CGS | 147.00 | 254.00 | 177.00 |
| rlr12.pk0025.e4:fis | FIS | 117.00 | 102.00 | 100.00 |
| sgc5c.pk001.j9:fis | CGS | 149.00 | >254.00 | >254.00 |
| wdk4c.pk006.m9:fis | CGS | >254.00 | 155.00 | 151.00 |

FIGS. 2A–2C present an alignment of the amino acid sequences set forth in SEQ ID NOs:32, 34, 36, and 38 and the *Hordeum vulgare, Daucus carota*, and *Arabidopsis thaliana* sequences (SEQ ID NO:41, SEQ ID NO:42, and SEQ ID NO:43, respectively). The data in Table 8 represents a calculation of the percent identity of the amino acid sequences set forth in SEQ ID NOs:18, 32, 34, 36, and 38 and the *Hordeum vulgare, Daucus carota*, and *Arabidopsis thaliana* sequences (SEQ ID NO:41, SEQ ID NO:42, and SEQ ID NO:43, respectively).

TABLE 8

Percent Identity of Amino Acid Sequences Deduced From the
Nucleotide Sequences of cDNA Clones Encoding Polypeptides
Homologous to 4-Hydroxyphenylpyruvate Dioxygenase

| | Percent Identity to | | |
|---|---|---|---|
| SEQ ID NO. | 3334222 | 3334219 | 3334223 |
| 18 | 49.4 | 58.2 | 60.0 |
| 32 | 58.5 | 73.3 | 67.4 |
| 34 | 86.4 | 73.3 | 69.9 |
| 36 | 49.4 | 58.2 | 60.0 |
| 38 | 94.2 | 59.9 | 58.1 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode substantial portions of rice, soybean, *Vernonia*, and wheat 4-hydroxyphenyl-pyruvate dioxygenase, and entire catalpa, soybean, and wheat 4-hydroxyphenylpyruvate dioxygenase. These sequences represent the first catalpa, rice, soybean, *Vernonia*, and wheat sequences encoding 4-hydroxyphenylpyruvate dioxygenase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189: 113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Evaluating Compounds for their Ability to Inhibit the Activity of Vitamin E Biosynthetic Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for gamma tocopherol methyltransferase are presented by d'Harlingue and Camara (1985) J. Biol. Chem. 260:15200–15203. Assays for 4-hydroxyphenylpyruvate dioxygenase are presented by Norris et al. (1995) Plant Cell 7: 2139–2149.

Example 9

Expression of Gamma Tocopherol Methyltransferase in Soybean Somatic Embryos

The ability to change the levels of alpha- and gamma-tocopherol in plants by transforming them with sequences encoding gamma tocopherol methyltransferase was tested by preparing transgenic soybean somatic embryos and assaying the tocopherol levels. Plasmid DNA from clone sah1c.pk001.k8 was used as a template to prepare a Not I pcr fragment encoding the entire deduced open reading frame using the following pcr primers (forward primer AGC GCG GCC GCA TGG CCA CCG TGG TGA GGA TCC CAA CAA TCT CAT GCA TCC ACA TCC ACA (SEQ ID NO:44); reverse primer AGC GCG GCC GCT TAT CTA GTG TGG AAA TAA TGA TCA (SEQ ID NO:45)). Standard pcr reactions were used (100 microliter total reaction containing 5 ng plasmid, 25 nmoles primer, 25 nmoles dNTPs, 1×cloned pfu buffer (Stratagene), 5% DMSO, 5U cloned pfu DNA polymerase (Stratagene). The recommended cycling parameters for pcr with pfu DNA polymerase were used (denature 45 s 94° C., anneal 45 s 55° C., extend 2.5 min 72° C., 25 cycles, final 10 min extension at 72° C.). The pcr product was purified on a 1% agarose/TAE gel (precast FMC), the ethidium bromide visualized band cut out and purified using a QIAquick gel extraction kit (Qiagen). The band prep (40 ng) was ligated into PCR Blunt (InVitrogen) according to the manufacturers recommendations, and the ligated plasmid used to transform E. coli DH 10 cells. Kanamycin resistant colonies were grown overnight in liquid culture (LB/Kan), plasmids prepared and cut with Not I. Plasmids containing the correct insert size were selected for full insert sequence to confirm fidelity of pcr.Plasmids containg the correct insert verified by DNA sequencing were digested with Not I and ligated to Not I-digested and phosphatase-treated pKS67. The plasmid pkS67 was prepared by replacing in pRB20 (described in U.S. Pat. No. 5,846,784) the 800 bp Nos 3' fragment, with the 285 bp Nos 3' fragment containing the polyadenylation signal sequence and described in Depicker et al. (1982) *J. Mol. Appl. Genet.* 1:561–573. Clones were screened for the sense and anti-sense orientation of the gamma tocopherol methyltransferase insert fragment by restriction enzyme digestion.

Transformation of Soybean Somatic Embryo Cultures

The following stock solutions and media were used for transformation and propagation of soybean somatic embryos:

| Stock Solutions | (g/L) |
|---|---|
| MS Sulfate 100× stock | |
| MgSO$_4$•7H$_2$O | 37.0 |
| MnSO$_4$•H$_2$O | 1.69 |
| ZnSO$_4$•7H$_2$O | 0.86 |
| CuSO$_4$•5H$_2$O | 0.0025 |
| MS Halides 100× stock | |
| CaCl$_2$•2H$_2$O | 44.0 |
| KI | 0.083 |
| CoCl$_2$•6H$_2$O | 0.00125 |
| KH$_2$PO$_4$ | 17.0 |
| H$_3$BO$_3$ | 0.62 |
| Na$_2$MoO$_4$•2H$_2$O | 0.025 |
| Na$_2$EDTA | 3.724 |
| FeSO$_4$•7H$_2$O | 2.784 |
| B5 Vitamin stock | |
| myo-inositol | 100.0 |
| nicotinic acid | 1.0 |
| pyridoxine HCl | 1.0 |
| thiamine | 10.0 |
| Media | |

SB55 (per Liter)

10 mL of each MS stock
1 mL of B5 Vitamin stock
0.8 g NH$_4$NO$_3$
3.033 g KNO$_3$
1 mL 2,4-D (10 mg/mL stock)
0.667 g asparagine
pH 5.7

SB103 (per Liter)

1 pk. Murashige & Skoog salt mixture*
60 g maltose
2 g gelrite
pH 5.7

SB148 (per Liter)

1 pk. Murashige & Skoog salt mixture*
60 g maltose
1 mL B5 vitamin stock
7 g agarose
pH 5.7

*(Gibco BRL)

Soybean embryonic suspension cultures were maintained in 35 mL liquid media (SB55) on a rotary shaker (150 rpm) at 28° C. with a mix of fluorescent and incandescent lights providing a 16 h day 8 h night cycle. Cultures were subcultured every 2 to 3 weeks by inoculating approximately 35 mg of tissue into 35 mL of fresh liquid media.

Soybean embryonic suspension cultures were transformed with the plasmid containing the gamma tocopherol methyltransferase sequence by the method of particle gun bombardment (see Klein et al. (1987) *Nature* 327:70–73) using a DuPont Biolistic PDS1000/He instrument. Five µL of pKS93s plasmid DNA (1 g/L), 50 µL CaCl$_2$ (2.5 M), and 20 µL spermidine (0.1 M) were added to 50 µL of a 60 mg/mL 1 mm gold particle suspension. The particle preparation was agitated for 3 minutes, spun on a microfuge for 10 seconds and the supernate removed. The DNA-coated particles were then washed once with 400 µL of 70% ethanol and resuspended in 40 µL of anhydrous ethanol. The DNA/particle suspension was sonicated three times for 1 second each. Five µL of the DNA-coated gold particles were then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, containing 0.5% charcoal to begin maturation. After 1 week, embryos were transferred to SB103 media minus charcoal. After 5 weeks on SB 103 media, maturing embryos were separated and placed onto SB148 media. During maturation embryos were kept at 26° C. with a mix of fluorescent and incandescent lights providing a 16 h day 8 h night cycle. After 3 weeks on SB148 media, embryos were analyzed for the expression of the tocopherols. Each embryonic cluster gave rise to 5 to 20 somatic embryos.

Non-transformed somatic embryos were cultured by the same method as used for the transformed somatic embryos.

Analysis of Transformed Somatic Embryos

At the end of the 6$^{th}$ week on SB148 medium somatic embryos were harvested from 25 independently transformed lines. Somatic embryos were collected in pools of five and wieghed for fresh weight. Excess embryos were stored in 96-well plates at −80°. The pooled somatic embryos were lyophilized for 18 hours and the dry weight measured. The lyophilized somatic embryos were briefly pulverised with a hand held Potter homogeniser and then 600 ul of heptane added and the samples incubated for 24 hours in the dark at room temperature to extract oils and tocopherols. The heptane was decanted and a further 300 ul added to the samples. The extracts were combined and centrifuged (5 min, 12000 g). The supernatant was stored in amber hplc autosampler vials at −20° C. prior to analysis.

HPLC analysis of the extracts was carried out using an HP1100 system (Agilent Technologies) 25 µl of the heptane sample was applied to a Lichrosphere Si 60 column (5 micron 4×12.5 mm). The column was eluted with heptane/isopropanol (98:2 v/v) at a flow rate of 1ml/min. After 6 minutes all four tocopherol isomers were eluted, as detected by a HP1100 fluorescence detector (Excitation wavelength 295 nm, emission wavelength 330 nm). Individual tocopherol standards (Matreya) were diluted with hplc grade heptane to levels between 1 and 200 ng/ul to construct a 6 point external standard curve. Tocopherols in each oil were quantified using a standard curve run on the same day as the samples. The sum of tocopherol peak areas of samples from a non-transformed control line were compared with those of 25 independent gamma tocopherol methyltransferase-transformed, hygromycin resistant lines. FIG. 3 shows a graph depicting the distribution of the percent alpha- and gamma-tocopherol of soybean somatic embryos transgenic for the gamma tocopherol methyltransferase gene and a control line. The mean alpha tocopherol content is 40 to 70%. Some lines, such as the ones represented in bars 2, 5, and 18 appear to represent overexpression of the gamma tocopherol methyltransferase, which would be predicted to yield higher levels of alpha tocopherol. Other lines, such as those represented in bars 6 and 10 appear to represent co-suppression of the gamma tocopherol methyltransferase since this is predicted to yield higher levels of gamma tocopherol. These results indicate that transgenic expression of gamma-tocopherol methyltransferase affords the ability to manipulate tocopherol levels as desired for a particular application.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising: (a) a nucleotide sequence encoding a gamma tocopherol methyltransferase having an amino acid sequence of at least 95% sequence identity, based on the Clustal method of alignment with pairwise alignment default parameters of KTUPLE=1, GAP PENALTY=3, WINDOW=5 and DIAGONALS SAVED=5, when compared to SEQ ID NO:22; or (b) the complement of the nucleotide sequence, wherein the complement and the nucleotide sequence have the same number of nucleotides and are 100% complementary.

2. The polynucleotide of claim 1, wherein the amino acid sequence of the gamma tocopherol methyltransferase comprises SEQ ID NO:22.

3. The polynucleotide of claim 1, wherein the polynucleotide comprises SEQ ID NO:21.

4. An isolated nucleic acid molecule that encodes a plant gamma tocopherol methyltransferase and remains hybridized with the isolated polynucleotide of claim 1 under a wash condition of 0.1×SSC, 0.1% SDS, and 65° C.

5. A recombinant DNA construct comprising the polynucleotide of claim 1 operably linked to at least one regulatory sequence.

6. The recombinant DNA construct of claim 5, wherein the recombinant DNA construct is an expression vector.

7. A host cell comprising the recombinant DNA construct of claim 5, wherein the cell is selected from the group consisting of a yeast cell, a bacterial cell, an insect cell, and a plant cell.

8. A transgenic plant comprising the recombinant DNA construct of claim 5.

9. A method for transforming a cell comprising introducing into a cell the recombinant DNA construct of claim 5.

10. A method for producing a transgenic plant comprising: (a) transforming a plant cell with the recombinant DNA construct of claim 5, and (b) regenerating a transgenic plant from the transformed plant cell.

11. A vector comprising the polynucleotide of claim 1.

* * * * *

SEQUENCE LISTING

```
<160> NUMBER OF SEQ ID NOS: 45

<210> SEQ ID NO 1
<211> LENGTH: 792
<212> TYPE: DNA
<213> ORGANISM: Zea mays
<220> FEATURE:
<221> NAME/KEY: unsure
<222> LOCATION: (586)
<223> OTHER INFORMATION: n= a, c, g, or t
<220> FEATURE:
<221> NAME/KEY: unsure
<222> LOCATION: (718)
<223> OTHER INFORMATION: n= a, c, g, or t
<220> FEATURE:
<221> NAME/KEY: unsure
<222> LOCATION: (762)
<223> OTHER INFORMATION: n= a, c, g, or t
<220> FEATURE:
<221> NAME/KEY: unsure
<222> LOCATION: (773)
<223> OTHER INFORMATION: n= a, c, g, or t
<220> FEATURE:
<221> NAME/KEY: unsure
<222> LOCATION: (782)
<223> OTHER INFORMATION: n= a, c, g, or t
<220> FEATURE:
<221> NAME/KEY: unsure
<222> LOCATION: (790)
<223> OTHER INFORMATION: n= a, c, g, or t

<400> SEQUENCE: 1
gttgagccct gttcaagccg agagaggaaa tgctctcgct gcagcgcagg ggttgtcgga      60
tcaggttact ctgcaagttg ctgatgctct ggagcaaccg tttcctgacg ggcagttcga     120
tctggtgtgg tccatggaga gtggcgagca catgccggac aagagaaagt ttgttagtga     180
gctagcacgc gtggcggctc ctggagggac aataatcatc gtgacatggt gccataggaa     240
cctggatcca tccgaaacct cgctaaagcc cgatgaactg agcctcctga ggaggatatg     300
cgacgcgtac tacctcccgg actggtgctc accttcagac tatgtgaaca ttgccaagtc     360
actgtctctc gaggatatca agacagctga ctggtcggag aacgtggccc cgttttggcc     420
cgccgtgata aaatcagcgc taacatggaa gggcttcacc tctctgctga cgaccggatg     480
gaagacgatc agaggcgcga tggtgatgcc gctaatgatc cagggctaca agaagggct     540 catcaaattc accatcatca cctgtcgcaa gcctggagcc gcgtangagg aggcaaggag     600
cacaagttac tagcacagca caggatgcaa gtgcatatgt agatcatggc acatcgccgt     660
cactcatcat actgcacaaa atcaaatctc caggacattt aataattctg cacctcanat     720
attcaggggg gccggtacca atcgccatat gatctatacc gnccacggcg tcnttaactc     780
tnacggaaan ct                                                          792
```

<210> SEQ ID NO 2
<211> LENGTH: 191
<212> TYPE: PRT
<213> ORGANISM: Zea mays

<400> SEQUENCE: 2

```
Leu Ser Pro Val Gln Ala Glu Arg Gly Asn Ala Leu Ala Ala Ala Gln
  1               5                  10                  15

Gly Leu Ser Asp Gln Val Thr Leu Gln Val Ala Asp Ala Leu Glu Gln
             20                  25                  30

Pro Phe Pro Asp Gly Gln Phe Asp Leu Val Trp Ser Met Glu Ser Gly
         35                  40                  45

Glu His Met Pro Asp Lys Arg Lys Phe Val Ser Glu Leu Ala Arg Val
     50                  55                  60

Ala Ala Pro Gly Gly Thr Ile Ile Val Thr Trp Cys His Arg Asn
 65                  70                  75                  80

Leu Asp Pro Ser Glu Thr Ser Leu Lys Pro Asp Leu Ser Leu Leu
                 85                  90                  95

Arg Arg Ile Cys Asp Ala Tyr Tyr Leu Pro Asp Trp Cys Ser Pro Ser
                100                 105                 110

Asp Tyr Val Asn Ile Ala Lys Ser Leu Ser Leu Glu Asp Ile Lys Thr
            115                 120                 125

Ala Asp Trp Ser Glu Asn Val Ala Pro Phe Trp Pro Ala Val Ile Lys
        130                 135                 140

Ser Ala Leu Thr Trp Lys Gly Phe Thr Ser Leu Leu Thr Thr Gly Trp
145                 150                 155                 160

Lys Thr Ile Arg Gly Ala Met Val Met Pro Leu Met Ile Gln Gly Tyr
                165                 170                 175

Lys Lys Gly Leu Ile Lys Phe Thr Ile Ile Thr Cys Arg Lys Pro
            180                 185                 190
```

<210> SEQ ID NO 3
<211> LENGTH: 521
<212> TYPE: DNA
<213> ORGANISM: Oryza sativa
<220> FEATURE:
<221> NAME/KEY: unsure
<222> LOCATION: (269)
<223> OTHER INFORMATION: n= a, c, g, or t
<220> FEATURE:
<221> NAME/KEY: unsure
<222> LOCATION: (274)
<223> OTHER INFORMATION: n= a, c, g, or t
<220> FEATURE:
<221> NAME/KEY: unsure
<222> LOCATION: (286)
<223> OTHER INFORMATION: n= a, c, g, or t
<220> FEATURE:
<221> NAME/KEY: unsure
<222> LOCATION: (302)
<223> OTHER INFORMATION: n= a, c, g, or t
<220> FEATURE:
<221> NAME/KEY: unsure
<222> LOCATION: (330)
<223> OTHER INFORMATION: n= a, c, g, or t
<220> FEATURE:
<221> NAME/KEY: unsure
<222> LOCATION: (381)..(382)
<223> OTHER INFORMATION: n= a, c, g, or t
<220> FEATURE:
<221> NAME/KEY: unsure
<222> LOCATION: (387)
<223> OTHER INFORMATION: n= a, c, g, or t
<220> FEATURE:

```
<221> NAME/KEY: unsure
<222> LOCATION: (398)
<223> OTHER INFORMATION: n= a, c, g, or t
<220> FEATURE:
<221> NAME/KEY: unsure
<222> LOCATION: (418)
<223> OTHER INFORMATION: n= a, c, g, or t
<220> FEATURE:
<221> NAME/KEY: unsure
<222> LOCATION: (429)
<223> OTHER INFORMATION: n= a, c, g, or t
<220> FEATURE:
<221> NAME/KEY: unsure
<222> LOCATION: (436)
<223> OTHER INFORMATION: n= a, c, g, or t
<220> FEATURE:
<221> NAME/KEY: unsure
<222> LOCATION: (462)
<223> OTHER INFORMATION: n= a, c, g, or t
<220> FEATURE:
<221> NAME/KEY: unsure
<222> LOCATION: (467)
<223> OTHER INFORMATION: n= a, c, g, or t
<220> FEATURE:
<221> NAME/KEY: unsure
<222> LOCATION: (473)
<223> OTHER INFORMATION: n= a, c, g, or t
<220> FEATURE:
<221> NAME/KEY: unsure
<222> LOCATION: (514)
<223> OTHER INFORMATION: n= a, c, g, or t

<400> SEQUENCE: 3
cttacagaca acggcagtt tgtaagcgag ctggcacgcg tcgcagctcc tggggcgaga      60
ataatcattg tgacctggtg ccataggaac ctcgagccat ccgaagagtc cctgaaacct    120
gatgagctga atctcctgaa aaggatatgc gatgcatatt atctcccaga ctggtgctct    180
ccttctgatt atgtcaaaat tgccgagtca ctgtctcttg aggatataag gacagctgat    240
tggtcaagag aacgtcgccc caatccggnc tgcnggttat taaataagc aattgacatg    300
gnaagggtta actttctcct ggctaagaan tgggtgggaa gacgattaag aaggtggaat    360
gggtgatgcc tccggatgat nnaaggntac aaagaaangg gtcaacaaat ttaacaanaa    420
caacctgtnc caaagnccccg aaacaacgca ataataccccc antaatnaaa ttncgctcct    480
ggctaacctt ctccaacaac gaattaatgg aaanttctga c                        521
```

<210> SEQ ID NO 4
<211> LENGTH: 82
<212> TYPE: PRT
<213> ORGANISM: Oryza sativa

<400> SEQUENCE: 4

```
Leu Thr Asp Lys Arg Gln Phe Val Ser Glu Leu Ala Arg Val Ala Ala
  1               5                  10                  15

Pro Gly Ala Arg Ile Ile Ile Val Thr Trp Cys His Arg Asn Leu Glu
             20                  25                  30

Pro Ser Glu Glu Ser Leu Lys Pro Asp Glu Leu Asn Leu Leu Lys Arg
         35                  40                  45

Ile Cys Asp Ala Tyr Tyr Leu Pro Asp Trp Cys Ser Pro Ser Asp Tyr
     50                  55                  60

Val Lys Ile Ala Glu Ser Leu Ser Leu Glu Asp Ile Arg Thr Ala Asp
 65                  70                  75                  80

Trp Ser
```

<210> SEQ ID NO 5

```
<211> LENGTH: 592
<212> TYPE: DNA
<213> ORGANISM: Oryza sativa
<220> FEATURE:
<221> NAME/KEY: unsure
<222> LOCATION: (295)
<223> OTHER INFORMATION: n= a, c, g, or t
<220> FEATURE:
<221> NAME/KEY: unsure
<222> LOCATION: (342)
<223> OTHER INFORMATION: n= a, c, g, or t
<220> FEATURE:
<221> NAME/KEY: unsure
<222> LOCATION: (491)
<223> OTHER INFORMATION: n= a, c, g, or t
<220> FEATURE:
<221> NAME/KEY: unsure
<222> LOCATION: (495)
<223> OTHER INFORMATION: n= a, c, g, or t
<220> FEATURE:
<221> NAME/KEY: unsure
<222> LOCATION: (519)
<223> OTHER INFORMATION: n= a, c, g, or t
<220> FEATURE:
<221> NAME/KEY: unsure
<222> LOCATION: (549)
<223> OTHER INFORMATION: n= a, c, g, or t

<400> SEQUENCE: 5
cttacatgta agctcgtgcc gaattcggca cgagcttaca aaatggccca cgccgccgcg      60
gccacgggcg cactggcacc gctgcatcca ctgctccgct gcacgagccg tcatctctgc    120
gcctcggctt cccctcgcgc cggcctctgc ctccaccacc accgccgccg ccgccgcagc    180
agccggagga cgaaactcgc cgtgcgcgcg atggcaccga cgttgtcctc gtcgtcgacg    240
gcggcggcag ctcccccggg gctgaaggag ggcatcgcgg ggctctacga cgaancgtcc    300
ggcgtgtggg agagcatctg gggcgagcac atgcaccacg gnttctacga cgccggcgag    360
ggcgcctcca tgtccgacca ccgccgcgcc ccagttcgca tgatcgagga cctcgccttc    420
gccgcctccc cgatgatcgg agaagaacca aaatgtattg atttggtgtg gattggtggt    480
actcaagata ntggngaaca atacggacgc atgctacgna tacttgatcg gtgcaggtga    540
aagagaaanc ctcgcgcaga caaggtatag caagtccctt taagttgtat ga            592

<210> SEQ ID NO 6
<211> LENGTH: 144
<212> TYPE: PRT
<213> ORGANISM: Oryza sativa
<220> FEATURE:
<221> NAME/KEY: UNSURE
<222> LOCATION: (99)
<223> OTHER INFORMATION: Xaa = ANY AMINO ACID

<400> SEQUENCE: 6

Leu Thr Cys Lys Leu Val Pro Asn Ser Ala Arg Ala Tyr Lys Met Ala
 1               5                  10                  15

His Ala Ala Ala Thr Gly Ala Leu Ala Pro Leu His Pro Leu Leu
            20                  25                  30

Arg Cys Thr Ser Arg His Leu Cys Ala Ser Ala Ser Pro Arg Ala Gly
        35                  40                  45

Leu Cys Leu His His His Arg Arg Arg Arg Ser Ser Arg Arg Thr
    50                  55                  60

Lys Leu Ala Val Arg Ala Met Ala Pro Thr Leu Ser Ser Ser Ser Thr
65                  70                  75                  80

Ala Ala Ala Ala Pro Pro Gly Leu Lys Glu Gly Ile Ala Gly Leu Tyr
                85                  90                  95
```

```
Asp Glu Xaa Ser Gly Val Trp Glu Ser Ile Trp Gly Glu His Met His
            100                 105                 110

His Gly Phe Tyr Asp Ala Gly Glu Gly Ala Ser Met Ser Asp His Arg
        115                 120                 125

Arg Ala Pro Val Arg Met Ile Glu Asp Leu Ala Phe Ala Ala Ser Pro
    130                 135                 140
```

<210> SEQ ID NO 7
<211> LENGTH: 1331
<212> TYPE: DNA
<213> ORGANISM: Glycine max

<400> SEQUENCE: 7

```
gtgacatggc caccgtggtg aggatcccaa caatctcatg catccacatc cacacgttcc     60
gttcccaatc ccctcgcact ttcgccagaa tccgggtcgg acccaggtcg tgggctccta    120
ttcgggcatc ggcagcgagc tcggagagag gggagatagt attggagcag aagccgaaga    180
aggatgacaa gaagaagctg cagaagggaa tcgcagagtt ttacgacgag tcgtctggct    240
tatgggagaa catttggggc gaccacatgc accatggctt tatgactcg gattccactg     300
tttcgctttc ggatcatcgt gctgctcaga tccgaatgat ccaagagtct cttcgctttg    360
cctctgtttc tgaggagcgt agtaaatggc caagagtat agttgatgtt gggtgtggca    420
taggtggcag ctctagatac ctggccaaga aatttggagc aaccagtgta ggcatcactc    480
tgagtcctgt tcaagctcaa agagcaaatg ctcttgctgc tgctcaagga ttggctgata    540
aggtttcctt tcaggttgct gacgctctac agcaaccatt ctctgacggc cagtttgatc    600
tggtgtggtc catggagagt ggagagcata tgcctgacaa agctaagttt gttggagagt    660
tagctcgggt agcagcacca ggtgccatta ataatagt aacatggtgc cacagggatc     720
ttggccctga cgaacaatcc ttacatccat gggagcaaga tctcttaaag aagatttgcg    780
atgcatatta cctccctgcc tggtgctcaa cttctgatta tgttaagttg ctccaatccc    840
tgtcacttca ggacatcaag tcagaagatt ggtctcgctt tgttgctcca ttttggccag    900
cagtgatacg ctcagccttc acatggaagg gtctatcttc actcttgagc agtggtaagc    960
ttggaattta tattgcattt caaaaacaaa ccccccatc ttctattgca acttgcaagt    1020
cttatgtcac tgatcattat ttccacacta gataacccctt tacaactaag aacgtagtct   1080
tcatgttcag cgaaatagat aaaaatatgc aacagagtca gagacagggt gcatgatatt   1140
tacaagaaaa tatcttttat atatataaat gattcaatca aattacttga tgaggattat   1200
gagtgaaaat gagaggacag tcatagaaac tttatcctac attccttcta tttccacttc   1260
tgtcaaatat tcctttcatc ttagctatgc tacttgactt gagtaaaaaa aaaaaaaaaa   1320
aaaaaaaaa a                                                         1331
```

<210> SEQ ID NO 8
<211> LENGTH: 349
<212> TYPE: PRT
<213> ORGANISM: Glycine max

<400> SEQUENCE: 8

```
Met Ala Thr Val Val Arg Ile Pro Thr Ile Ser Cys Ile His Ile His
  1               5                  10                  15

Thr Phe Arg Ser Gln Ser Pro Arg Thr Phe Ala Arg Ile Arg Val Gly
             20                  25                  30

Pro Arg Ser Trp Ala Pro Ile Arg Ala Ser Ala Ala Ser Ser Glu Arg
```

```
            35                  40                  45
Gly Glu Ile Val Leu Glu Gln Lys Pro Lys Asp Asp Lys Lys
 50                  55                  60

Leu Gln Lys Gly Ile Ala Glu Phe Tyr Asp Ser Ser Gly Leu Trp
 65                  70                  75                  80

Glu Asn Ile Trp Gly Asp His Met His Gly Phe Tyr Asp Ser Asp
                 85                  90                  95

Ser Thr Val Ser Leu Ser Asp His Arg Ala Ala Gln Ile Arg Met Ile
                100                 105                 110

Gln Glu Ser Leu Arg Phe Ala Ser Val Ser Glu Arg Ser Lys Trp
        115                 120                 125

Pro Lys Ser Ile Val Asp Val Gly Cys Gly Ile Gly Gly Ser Ser Arg
    130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Gln Gly Leu
                165                 170                 175

Ala Asp Lys Val Ser Phe Gln Val Ala Asp Ala Leu Gln Gln Pro Phe
        180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
210                 215                 220

Pro Gly Ala Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
                260                 265                 270

Val Lys Leu Leu Gln Ser Leu Ser Leu Gln Asp Ile Lys Ser Glu Asp
        275                 280                 285

Trp Ser Arg Phe Val Ala Pro Phe Trp Pro Ala Val Ile Arg Ser Ala
        290                 295                 300

Phe Thr Trp Lys Gly Leu Ser Ser Leu Leu Ser Ser Gly Lys Leu Gly
305                 310                 315                 320

Ile Tyr Ile Ala Phe Gln Lys Gln Thr Pro Pro Ser Ser Ile Ala Thr
                325                 330                 335

Cys Lys Ser Tyr Val Thr Asp His Tyr Phe His Thr Arg
                340                 345

<210> SEQ ID NO 9
<211> LENGTH: 1011
<212> TYPE: DNA
<213> ORGANISM: Triticum aestivum
<220> FEATURE:
<221> NAME/KEY: unsure
<222> LOCATION: (385)
<223> OTHER INFORMATION: n= a, c, g, or t
<220> FEATURE:
<221> NAME/KEY: unsure
<222> LOCATION: (396)
<223> OTHER INFORMATION: n= a, c, g, or t
<220> FEATURE:
<221> NAME/KEY: unsure
<222> LOCATION: (909)
<223> OTHER INFORMATION: n= a, c, g, or t

<400> SEQUENCE: 9
```

```
acgagtcgtc cggcctgtgg gagagcatct ggggcgagca catgcaccac ggcttctacg    60
actccggcga ggccgcctcc atgtccgacc accgccgcgc ccagatccgc atgatcgagg   120
aggccctcgc cttcgccgcc gtccccgacg atccgacaaa caaacccaaa acgattgttg   180
atgttggatg cggaatcggt ggtagctcaa gatacctggg cgaacaaata tggagcacaa   240
tgctctggga tcacattgac ccagtgcaag ctgagagagg aaatgccctc gcggcagcgc   300 aagggggttgt ccggacaagg ttctttccaa ttgctgatct ctgggagcaa ccatttcctg   360
gatgggcatt tgatcttgtc cgggnccatg ggagantggt gacacatgcc gaacaaacag   420
aagtttgtaa gcgagctggc acgcgtcgca gctccaggag caactatcat catcgtgacc   480
tggtgccata ggaacctcgc gccatcggag gactcactga acctgacga gctgaatctt   540 ttgaaaaga tttgtgatgc atattacctc ccggattggg gctctccctc ggattatgtc   600
aagattgccg agtcattgtc tcttgaggat atcaaaacgg ccgactggtc tgaaaacgtg   660
gccccgttct ggcctgctgt catccaatca gcactgacat ggaaaggcct cacttctcta   720
ctaaggagtg gatggaagac gataaaggga gcactggtga tgcctctcat gatccaaggc   780
tacaagaaag gcctcattaa gttcaagcat catcacctgc cacaaacccc aagcagccat   840
agaaggagaa cctggaggcc gcatcgccca agagtggtag aatagaacca tgtgattgga   900
atagactcng cttgctgtcg ccttggtagc tgaataattc gtgttaccgt gcctctgtat   960
ctgcaactgg aagtgccata tgagaatggt tcctaaaagc aaaatctcct c            1011
```

<210> SEQ ID NO 10
<211> LENGTH: 293
<212> TYPE: PRT
<213> ORGANISM: Triticum aestivum
<220> FEATURE:
<221> NAME/KEY: UNSURE
<222> LOCATION: (127) (133)
<223> OTHER INFORMATION: Xaa = ANY AMINO ACID

<400> SEQUENCE: 10

```
Glu Ser Ser Gly Leu Trp Glu Ser Ile Trp Gly Glu His Met His His
  1               5                  10                  15

Gly Phe Tyr Asp Ser Gly Glu Ala Ala Ser Met Ser Asp His Arg Arg
             20                  25                  30

Ala Gln Ile Arg Met Ile Glu Glu Ala Leu Ala Phe Ala Ala Val Pro
         35                  40                  45

Asp Asp Pro Thr Asn Lys Pro Lys Thr Ile Val Asp Val Gly Cys Gly
     50                  55                  60

Ile Gly Gly Ser Ser Arg Tyr Leu Gly Glu Gln Ile Trp Ser Thr Met
 65                  70                  75                  80

Leu Trp Asp His Ile Asp Pro Val Gln Ala Glu Arg Gly Asn Ala Leu
                 85                  90                  95

Ala Ala Ala Gln Gly Val Val Arg Thr Arg Phe Phe Pro Ile Ala Asp
            100                 105                 110

Leu Trp Glu Gln Pro Phe Pro Gly Trp Ala Phe Asp Leu Val Xaa Xaa
        115                 120                 125

Xaa Xaa Xaa Xaa Xaa His Met Pro Asn Lys Gln Lys Phe Val Ser Glu
    130                 135                 140

Leu Ala Arg Val Ala Ala Pro Gly Ala Thr Ile Ile Val Thr Trp
145                 150                 155                 160

Cys His Arg Asn Leu Ala Pro Ser Glu Asp Ser Leu Lys Pro Asp Glu
                165                 170                 175
```

```
Leu Asn Leu Leu Lys Lys Ile Cys Asp Ala Tyr Tyr Leu Pro Asp Trp
            180                 185                 190

Cys Ser Pro Ser Asp Tyr Val Lys Ile Ala Glu Ser Leu Ser Leu Glu
        195                 200                 205

Asp Ile Lys Thr Ala Asp Trp Ser Glu Asn Val Ala Pro Phe Trp Pro
    210                 215                 220

Ala Val Ile Gln Ser Ala Leu Thr Trp Lys Gly Leu Thr Ser Leu Leu
225                 230                 235                 240

Arg Ser Gly Trp Lys Thr Ile Lys Gly Ala Leu Val Met Pro Leu Met
                245                 250                 255

Ile Gln Gly Tyr Lys Lys Gly Leu Ile Lys Phe Lys His His His Leu
                260                 265                 270

Pro Gln Thr Pro Ser Ser His Arg Arg Thr Trp Arg Pro His Arg
            275                 280                 285

Pro Arg Val Val Glu
    290
```

<210> SEQ ID NO 11
<211> LENGTH: 432
<212> TYPE: DNA
<213> ORGANISM: Oryza sativa
<220> FEATURE:
<221> NAME/KEY: unsure
<222> LOCATION: (361)
<223> OTHER INFORMATION: n= a, c, g, or t
<220> FEATURE:
<221> NAME/KEY: unsure
<222> LOCATION: (368)
<223> OTHER INFORMATION: n= a, c, g, or t
<220> FEATURE:
<221> NAME/KEY: unsure
<222> LOCATION: (401)
<223> OTHER INFORMATION: n= a, c, g, or t
<220> FEATURE:
<221> NAME/KEY: unsure
<222> LOCATION: (448)
<223> OTHER INFORMATION: n= a, c, g, or t
<220> FEATURE:
<221> NAME/KEY: unsure
<222> LOCATION: (428)
<223> OTHER INFORMATION: n= a, c, g, or t

<400> SEQUENCE: 11
ccacgtcgag ctctggtgcg ccgacgccgc gtccgccgcg ggccggttcg ccttcgccct      60
gggcgcgccg ctcgccgcca ggtccgacct ctccacgggg aactccgcgc acgcctccct     120
cctcctccgc tccgcctccg tcgcgttcct cttcaccgcc ccctacggcg cgaccacgg      180 cgtcggcgcg gacgcggcca ccaccgcctc catcccttcc ttctcccctt cctttctccc     240
cgctcctgga tcaggccaca ggaggggagc gatggtggag cggcaccg taggcggcgg       300 aggtggcgtt cctcctcccct agctcccaga cccggctgga ggaggagtg atggtggcgg     360 naggcggngc tccctcctct ccctccctcc tcctcacaat ntggccggag ggaggaaggg     420
gccgcggncc aa                                                         432

<210> SEQ ID NO 12
<211> LENGTH: 75
<212> TYPE: PRT
<213> ORGANISM: Oryza sativa

<400> SEQUENCE: 12

```
His Val Glu Leu Trp Cys Ala Asp Ala Ala Ser Ala Ala Gly Arg Phe
  1               5                  10                  15
```

```
Ala Phe Ala Leu Gly Ala Pro Leu Ala Ala Arg Ser Asp Leu Ser Thr
            20                  25                  30

Gly Asn Ser Ala His Ala Ser Leu Leu Arg Ser Ala Ser Val Ala
            35                  40                  45

Phe Leu Phe Thr Ala Pro Tyr Gly Gly Asp His Gly Val Gly Ala Asp
    50                  55                  60

Ala Ala Thr Thr Ala Ser Ile Pro Ser Phe Ser
65                  70                  75

<210> SEQ ID NO 13
<211> LENGTH: 628
<212> TYPE: DNA
<213> ORGANISM: Oryza sativa
<220> FEATURE:
<221> NAME/KEY: unsure
<222> LOCATION: (315)
<223> OTHER INFORMATION: n= a, c, g, or t
<220> FEATURE:
<221> NAME/KEY: unsure
<222> LOCATION: (325)
<223> OTHER INFORMATION: n= a, c, g, or t
<220> FEATURE:
<221> NAME/KEY: unsure
<222> LOCATION: (395)
<223> OTHER INFORMATION: n= a, c, g, or t
<220> FEATURE:
<221> NAME/KEY: unsure
<222> LOCATION: (438)
<223> OTHER INFORMATION: n= a, c, g, or t
<220> FEATURE:
<221> NAME/KEY: unsure
<222> LOCATION: (472)
<223> OTHER INFORMATION: n= a, c, g, or t
<220> FEATURE:
<221> NAME/KEY: unsure
<222> LOCATION: (488)
<223> OTHER INFORMATION: n= a, c, g, or t
<220> FEATURE:
<221> NAME/KEY: unsure
<222> LOCATION: (491) (492)
<223> OTHER INFORMATION: n= a, c, g, or t
<220> FEATURE:
<221> NAME/KEY: unsure
<222> LOCATION: (502)
<223> OTHER INFORMATION: n= a, c, g, or t
<220> FEATURE:
<221> NAME/KEY: unsure
<222> LOCATION: (526)
<223> OTHER INFORMATION: n= a, c, g, or t
<220> FEATURE:
<221> NAME/KEY: unsure
<222> LOCATION: (535)
<223> OTHER INFORMATION: n= a, c, g, or t
<220> FEATURE:
<221> NAME/KEY: unsure
<222> LOCATION: (537)
<223> OTHER INFORMATION: n= a, c, g, or t
<220> FEATURE:
<221> NAME/KEY: unsure
<222> LOCATION: (346)
<223> OTHER INFORMATION: n= a, c, g, or t
<220> FEATURE:
<221> NAME/KEY: unsure
<222> LOCATION: (563)
<223> OTHER INFORMATION: n= a, c, g, or t
<220> FEATURE:
<221> NAME/KEY: unsure
<222> LOCATION: (582)
<223> OTHER INFORMATION: n= a, c, g, or t
<220> FEATURE:
<221> NAME/KEY: unsure
<222> LOCATION: (590)
<223> OTHER INFORMATION: n= a, c, g, or t
<220> FEATURE:
<221> NAME/KEY: unsure
```

```
<222> LOCATION: (602)
<223> OTHER INFORMATION: n= a, c, g, or t
<220> FEATURE:
<221> NAME/KEY: unsure
<222> LOCATION: (617)
<223> OTHER INFORMATION: n= a, c, g, or t
<220> FEATURE:
<221> NAME/KEY: unsure
<222> LOCATION: (620)
<223> OTHER INFORMATION: n= a, c, g, or t
<220> FEATURE:
<221> NAME/KEY: unsure
<222> LOCATION: (623)
<223> OTHER INFORMATION: n= a, c, g, or t

<400> SEQUENCE: 13
gaagagctac ggcctccgcc ggttcgacca cgtcgtcggc aacgtgccgg agctcgctcc        60
ggtagccgcg tacatctccg ggttcaccgg gttccacgag ttcgccgagt tcaccgccga      120
ggacgtgggc accgccgaga gcggcctcaa ctcggtggtg ctcgccaaca acgcggagac      180
cgtgctgctg ccgctcaacg agccggtgca cggcaccaag cggcggagcc agatacagac      240
gtacctggac caccacggcg gcccgggggt gcagcacatc gcgctggcca gcgacgacgt      300
gctcgggacg ctgangggaga tgccnggcgc ctccgcatgg gcggttcgat tcttgggccc      360
gccgccgcca actactacga cggctgcgcg gcgcnccggg acttctctcg ggagagcaat      420
taacaatgcc aagactcngg tgtcctggac aaggatacaa gggtttccaa tnttaacaag      480
cattgaanag nnactttctg gngagatcaa gatggtgatg aaagtnaatg gaagntncaa      540
aggggntcgc ggttggaaga atntcggctt aatcataggg tngaaacctn agcacagcct      600 antttaggtca gagatgngcn ganaaatt                                         628

<210> SEQ ID NO 14
<211> LENGTH: 123
<212> TYPE: PRT
<213> ORGANISM: Oryza sativa
<220> FEATURE:
<221> NAME/KEY: UNSURE
<222> LOCATION: (103)
<223> OTHER INFORMATION: Xaa = ANY AMINO ACID

<400> SEQUENCE: 14

Tyr Gly Leu Arg Arg Phe Asp His Val Val Gly Asn Val Pro Glu Leu
  1               5                  10                  15

Ala Pro Val Ala Ala Tyr Ile Ser Gly Phe Thr Gly Phe His Glu Phe
             20                  25                  30

Ala Glu Phe Thr Ala Glu Asp Val Gly Thr Ala Glu Ser Gly Leu Asn
         35                  40                  45

Ser Val Val Leu Ala Asn Asn Ala Glu Thr Val Leu Leu Pro Leu Asn
     50                  55                  60

Glu Pro Val His Gly Thr Lys Arg Arg Ser Gln Ile Gln Thr Tyr Leu
 65                  70                  75                  80

Asp His His Gly Gly Pro Gly Val Gln His Ile Ala Leu Ala Ser Asp
                 85                  90                  95

Asp Val Leu Gly Thr Leu Xaa Glu Met Pro Gly Ala Ser Ala Trp Ala
            100                 105                 110

Val Arg Phe Leu Gly Pro Pro Pro Thr Thr
            115                 120

<210> SEQ ID NO 15
<211> LENGTH: 1027
<212> TYPE: DNA
```

```
<213> ORGANISM: Glycine max
<220> FEATURE:
<221> NAME/KEY: unsure
<222> LOCATION: (617)
<223> OTHER INFORMATION: n= a, c, g, or t
<220> FEATURE:
<221> NAME/KEY: unsure
<222> LOCATION: (829)
<223> OTHER INFORMATION: n= a, c, g, or t
<220> FEATURE:
<221> NAME/KEY: unsure
<222> LOCATION: (841)
<223> OTHER INFORMATION: n= a, c, g, or t
<220> FEATURE:
<221> NAME/KEY: unsure
<222> LOCATION: (876)
<223> OTHER INFORMATION: n= a, c, g, or t
<220> FEATURE:
<221> NAME/KEY: unsure
<222> LOCATION: (911)
<223> OTHER INFORMATION: n= a, c, g, or t
<220> FEATURE:
<221> NAME/KEY: unsure
<222> LOCATION: (918) (919)
<223> OTHER INFORMATION: n= a, c, g, or t
<220> FEATURE:
<221> NAME/KEY: unsure
<222> LOCATION: (927)
<223> OTHER INFORMATION: n= a, c, g, or t
<220> FEATURE:
<221> NAME/KEY: unsure
<222> LOCATION: (936)
<223> OTHER INFORMATION: n= a, c, g, or t
<220> FEATURE:
<221> NAME/KEY: unsure
<222> LOCATION: (938)
<223> OTHER INFORMATION: n= a, c, g, or t
<220> FEATURE:
<221> NAME/KEY: unsure
<222> LOCATION: (969)
<223> OTHER INFORMATION: n= a, c, g, or t
<220> FEATURE:
<221> NAME/KEY: unsure
<222> LOCATION: (979)
<223> OTHER INFORMATION: n= a, c, g, or t
<220> FEATURE:
<221> NAME/KEY: unsure
<222> LOCATION: (981)
<223> OTHER INFORMATION: n= a, c, g, or t
<220> FEATURE:
<221> NAME/KEY: unsure
<222> LOCATION: (992)
<223> OTHER INFORMATION: n= a, c, g, or t
<220> FEATURE:
<221> NAME/KEY: unsure
<222> LOCATION: (1004)
<223> OTHER INFORMATION: n= a, c, g, or t
<220> FEATURE:
<221> NAME/KEY: unsure
<222> LOCATION: (1012)
<223> OTHER INFORMATION: n= a, c, g, or t
<220> FEATURE:
<221> NAME/KEY: unsure
<222> LOCATION: (1017)
<223> OTHER INFORMATION: n= a, c, g, or t

<400> SEQUENCE: 15
tcacaccaca ccaatgccaa tacccatgtg caacgaaatt caagcccaag cccaagccca    60
agcccaagcc caacctgggt ttaagctcgt cggtttcaaa acttcgtcc gaaccaatcc    120 taagtcggac cgctttcaag tcaaccgctt ccaccacatc gagttctggt gcaccgatgc    180
caccaacgcc tctcgccgat tctcttgggg acttggaatg cctattgtgg caaaatctga    240
tctctccacc ggaaaccaaa tccacgcctc ctacctcctc cgctccggcg acctctcctt    300
cctcttctcc gctccttact ctccctctct ctccgccggc tcctccgctg cctcctccgc    360
```

-continued

```
ctccattccc agtttcgacg ccgccacctg ccttgccttc gctgccaaac acggcttcgg    420
cgtccgcgcc atcgccttgg aagtcgccga cgcggaagcc gctttcagcg ccagcgtcgc    480
gaaaggagcc gagccggcgt cgccgccggt tctcgtcgac gatcgcaccg gcttcgcgga    540
ggtgcgcctc tacggcgacg tggtgctccg ctacgtcagc tacaaggacg ccgcgccgca    600
ggcgccacac gcagatncgt cgcggtggtt cctgccggga ttcgaggccg cggcgtcgtc    660
gtcttcgttt ccggagctgg actacgggat ccggcggctg gaccacgccg tcgggaacgt    720
tccggagctg cgccggcgg tgaggtacct gaaaggcttc agcggattcc acgagttcgc    780
ggagttcacc gcggaggacg tgggaacgag cgagagcggg ttgaactcng tggttctggc    840
ngaacaactc ggagacggtg ttgctgccgc tgaacnagcc cggtttacgg aacgaaagag    900
gaagaagcca nattgagnnc gtatttngaa cacaancaa aggtgcttgg tgtgcagcaa     960
ccttgcgcnt tgttactcnc naacatcttc ancacactga ggangagatg anaaaanccg   1020
acgtttg                                                             1027
```

<210> SEQ ID NO 16
<211> LENGTH: 276
<212> TYPE: PRT
<213> ORGANISM: Glycine max
<220> FEATURE:
<221> NAME/KEY: UNSURE
<222> LOCATION: (202)
<223> OTHER INFORMATION: Xaa = ANY AMINO ACID

<400> SEQUENCE: 16

```
Met Pro Ile Pro Met Cys Asn Glu Ile Gln Ala Gln Ala Gln Ala Gln
 1               5                  10                  15

Ala Gln Ala Gln Pro Gly Phe Lys Leu Val Gly Phe Lys Asn Phe Val
            20                  25                  30

Arg Thr Asn Pro Lys Ser Asp Arg Phe Gln Val Asn Arg Phe His His
        35                  40                  45

Ile Glu Phe Trp Cys Thr Asp Ala Thr Asn Ala Ser Arg Arg Phe Ser
    50                  55                  60

Trp Gly Leu Gly Met Pro Ile Val Ala Lys Ser Asp Leu Ser Thr Gly
65                  70                  75                  80

Asn Gln Ile His Ala Ser Tyr Leu Leu Arg Ser Gly Asp Leu Ser Phe
                85                  90                  95

Leu Phe Ser Ala Pro Tyr Ser Pro Ser Leu Ser Ala Gly Ser Ser Ala
            100                 105                 110

Ala Ser Ser Ala Ser Ile Pro Ser Phe Asp Ala Ala Thr Cys Leu Ala
        115                 120                 125

Phe Ala Ala Lys His Gly Phe Gly Val Arg Ala Ile Ala Leu Glu Val
    130                 135                 140

Ala Asp Ala Glu Ala Ala Phe Ser Ala Ser Val Ala Lys Gly Ala Glu
145                 150                 155                 160

Pro Ala Ser Pro Pro Val Leu Val Asp Asp Arg Thr Gly Phe Ala Glu
                165                 170                 175

Val Arg Leu Tyr Gly Asp Val Val Leu Arg Tyr Val Ser Tyr Lys Asp
            180                 185                 190

Ala Ala Pro Gln Ala Pro His Ala Asp Xaa Ser Arg Trp Phe Leu Pro
        195                 200                 205

Gly Phe Glu Ala Ala Ala Ser Ser Ser Phe Pro Glu Leu Asp Tyr
    210                 215                 220
```

```
Gly Ile Arg Arg Leu Asp His Ala Val Gly Asn Val Pro Glu Leu Ala
225                 230                 235                 240

Pro Ala Val Arg Tyr Leu Lys Gly Phe Ser Gly Phe His Glu Phe Ala
            245                 250                 255

Glu Phe Thr Ala Glu Asp Val Gly Thr Ser Gly Ser Gly Leu Asn Ser
        260                 265                 270

Val Val Leu Ala
        275

<210> SEQ ID NO 17
<211> LENGTH: 511
<212> TYPE: DNA
<213> ORGANISM: Vernonia mesipifolia
<220> FEATURE:
<221> NAME/KEY: unsure
<222> LOCATION: (494)
<223> OTHER INFORMATION: n= a, c, g, or t

<400> SEQUENCE: 17
ccacaccgat tgccggaact tcaccgcctc tcacggcctt gcagtccgag caatcgccat      60
tgaagtcgat gacgccgaat tagctttctc cgtcagcgtc tctcacggcg ctaaaccctc     120
cgctgctcct gtaacccttg gaaacaacga cgtcgtattg tctgaagtta agctttacgg     180
cgatgtcgct ttccggtaca taagttacaa aaatccgaac tatacatctt ccttttttgcc   240
cgggttcgag cccgttgaaa agacgtcgtc gttttatgac cttgactacg gtatccgccg     300
tttggaccac gccgtaggaa cgtccctgag cttgcttcgg cagtggacta cgtgaaatca     360
ttcaccggat tccatgagtt cgccgaattc accgcggagg acgtcgggac gagcgagagg     420
gaactgaatt cggtcgtttt agcttgcaac agtgagatgg tcttgattcc gatgaacgag     480
ccggtgtacg gaanaaaagg aagagccaga t                                    511

<210> SEQ ID NO 18
<211> LENGTH: 170
<212> TYPE: PRT
<213> ORGANISM: Vernonia mesipifolia
<220> FEATURE:
<221> NAME/KEY: UNSURE
<222> LOCATION: (165)
<223> OTHER INFORMATION: Xaa = ANY AMINO ACID

<400> SEQUENCE: 18

His Thr Asp Cys Arg Asn Phe Thr Ala Ser His Gly Leu Ala Val Arg
 1               5                  10                  15

Ala Ile Ala Ile Glu Val Asp Asp Ala Glu Leu Ala Phe Ser Val Ser
            20                  25                  30

Val Ser His Gly Ala Lys Pro Ser Ala Pro Val Thr Leu Gly Asn
        35                  40                  45

Asn Asp Val Val Leu Ser Glu Val Lys Leu Tyr Gly Asp Val Ala Phe
 50                  55                  60

Arg Tyr Ile Ser Tyr Lys Asn Pro Asn Tyr Thr Ser Ser Phe Leu Pro
65                  70                  75                  80

Gly Phe Glu Pro Val Glu Lys Thr Ser Ser Phe Tyr Asp Leu Asp Tyr
                85                  90                  95

Gly Ile Arg Arg Leu Asp His Ala Val Gly Asn Val Pro Glu Leu Ala
            100                 105                 110

Ser Ala Val Asp Tyr Val Lys Ser Phe Thr Gly Phe His Glu Phe Ala
        115                 120                 125

Glu Phe Thr Ala Glu Asp Val Gly Thr Ser Glu Arg Glu Leu Asn Ser
```

-continued

```
                130                 135                 140
Val Val Leu Ala Cys Asn Ser Glu Met Val Leu Ile Pro Met Asn Glu
145                 150                 155                 160

Pro Val Tyr Gly Xaa Lys Gly Arg Ala Arg
                165                 170

<210> SEQ ID NO 19
<211> LENGTH: 1165
<212> TYPE: DNA
<213> ORGANISM: Triticum aestivum
<220> FEATURE:
<221> NAME/KEY: unsure
<222> LOCATION: (567)
<223> OTHER INFORMATION: n= a, c, g, or t
<220> FEATURE:
<221> NAME/KEY: unsure
<222> LOCATION: (596)
<223> OTHER INFORMATION: n= a, c, g, or t
<220> FEATURE:
<221> NAME/KEY: unsure
<222> LOCATION: (627)
<223> OTHER INFORMATION: n= a, c, g, or t
<220> FEATURE:
<221> NAME/KEY: unsure
<222> LOCATION: (639)
<223> OTHER INFORMATION: n= a, c, g, or t
<220> FEATURE:
<221> NAME/KEY: unsure
<222> LOCATION: (655)
<223> OTHER INFORMATION: n= a, c, g, or t
<220> FEATURE:
<221> NAME/KEY: unsure
<222> LOCATION: (697)
<223> OTHER INFORMATION: n= a, c, g, or t
<220> FEATURE:
<221> NAME/KEY: unsure
<222> LOCATION: (709)
<223> OTHER INFORMATION: n= a, c, g, or t
<220> FEATURE:
<221> NAME/KEY: unsure
<222> LOCATION: (1039)
<223> OTHER INFORMATION: n= a, c, g, or t
<220> FEATURE:
<221> NAME/KEY: unsure
<222> LOCATION: (1066)
<223> OTHER INFORMATION: n= a, c, g, or t
<220> FEATURE:
<221> NAME/KEY: unsure
<222> LOCATION: (1126)
<223> OTHER INFORMATION: n= a, c, g, or t
<220> FEATURE:
<221> NAME/KEY: unsure
<222> LOCATION: (1152)
<223> OTHER INFORMATION: n= a, c, g, or t

<400> SEQUENCE: 19
caagaagcga acacacacca tgccgcccac cccaccacc cccgcagcca ccggcgccgc     60
cgcggtgacg ccggagcacg cgcggccgcg ccgaatggtc cgcttcaacc cgcgcagcga    120
ccgcttccac acgctcgcct tccaccacgt cgagttctgg tgcgcggacg ccgcctccgc    180
cgccggccgc ttcgccttcg cgctcggcgc gccgctcgcc gccaggtccg acctctccac    240
ggggaactcc gtgcacgcct cccagctgct ccgctcgggc aacctcgcct tcctcttcac    300
cgcgccctac gccaacggct gcgacgccgc caccgcctcc ctgccctcct tctccgccga    360
cgccgcgcgc cggttctccg cggaccacgg gctcgcggtg cgctccatag cgctgcgcgt    420
cgcggacgcc gccgaggcct tccgcgccag cgtcgacggg ggcgcgcgcc cggccttcag    480
ccccgtggac ctcggccgcg gcttcggctt tgcggaggtc gagctctacg cgacgtcgt    540 gctccgcttc gtcagcatcc ggacggnacg gacgtgcctt cttgccgggg ttcganggcg    600
```

```
ttgagcaacc gggtgccgtg gactaaggc tgacacggnt tgacacgttg tccgnaagtc    660
cggagcttgc ttcggcgccg cctaacgtag ccggctnaac gggttcaana attcgccagt    720
taacacggag gacgtgggca cggccgagag cgggctcaac tcgatggtgc tcgccaacaa    780
ctcggagggc gtgctgctgc cgctcaacga gccggtgcac ggcaccaagc gccggagcca    840
gatacagacg ttcctggaac accacggcgg ctcgggcgtg cagcacatcg cggtggccag    900
cagcgacgtg ctcaggacgc tcagggagat gcgtgcgcgc tccgccatgg gcggcttcga    960
cttcctgcca ccccgctgc cgaagtacta cgaaggcgtg cggcgcatcg ccggggatgt   1020
gctctcggag gcgcaaatna aggaatgcaa gaactggggg tgctcntcca caaggaagaa   1080
caaagggtgt tgctacaaat cctcaacaag ccaatntggg acaagccgac ttgttcctgg   1140
agatattcac angatctggt gcatg                                          1165
```

```
<210> SEQ ID NO 20
<211> LENGTH: 179
<212> TYPE: PRT
<213> ORGANISM: Triticum aestivum

<400> SEQUENCE: 20
```

```
Met Pro Pro Thr Pro Thr Thr Pro Ala Ala Thr Gly Ala Ala Ala Val
  1               5                  10                  15

Thr Pro Glu His Ala Arg Pro Arg Arg Met Val Arg Phe Asn Pro Arg
             20                  25                  30

Ser Asp Arg Phe His Thr Leu Ala Phe His His Val Glu Phe Trp Cys
         35                  40                  45

Ala Asp Ala Ala Ser Ala Ala Gly Arg Phe Ala Phe Ala Leu Gly Ala
     50                  55                  60

Pro Leu Ala Ala Arg Ser Asp Leu Ser Thr Gly Asn Ser Val His Ala
 65                  70                  75                  80

Ser Gln Leu Leu Arg Ser Gly Asn Leu Ala Phe Leu Phe Thr Ala Pro
                 85                  90                  95

Tyr Ala Asn Gly Cys Asp Ala Ala Thr Ala Ser Leu Pro Ser Phe Ser
            100                 105                 110

Ala Asp Ala Ala Arg Arg Phe Ser Ala Asp His Gly Leu Ala Val Arg
        115                 120                 125

Ser Ile Ala Leu Arg Val Ala Asp Ala Ala Glu Ala Phe Arg Ala Ser
    130                 135                 140

Val Asp Gly Gly Ala Arg Pro Ala Phe Ser Pro Val Asp Leu Gly Arg
145                 150                 155                 160

Gly Phe Gly Phe Ala Glu Val Glu Leu Tyr Gly Asp Val Val Leu Arg
                165                 170                 175

Phe Val Ser
```

```
<210> SEQ ID NO 21
<211> LENGTH: 1102
<212> TYPE: DNA
<213> ORGANISM: Zea mays
<220> FEATURE:
<221> NAME/KEY: unsure
<222> LOCATION: (454)
<223> OTHER INFORMATION: n = a, c, g, or t
<220> FEATURE:
<221> NAME/KEY: unsure
<222> LOCATION: (1072)
<223> OTHER INFORMATION: n = a, c, g, or t
<220> FEATURE:
<221> NAME/KEY: unsure
```

```
<222> LOCATION: (1083)
<223> OTHER INFORMATION: n = a, c, g, or t
<220> FEATURE:
<221> NAME/KEY: unsure
<222> LOCATION: (1092)
<223> OTHER INFORMATION: n = a, c, g, or t
<220> FEATURE:
<221> NAME/KEY: unsure
<222> LOCATION: (1100)
<223> OTHER INFORMATION: n = a, c, g, or t

<400> SEQUENCE: 21
atggctcacg cggcgctgct ccattgctcc cagtcctcca ggagcctcgc agcctgccgc      60
cgcggcagyc actaccgcgc cccttcgcac gtcccgcgcc actcccgccg tctccgacgc     120
gccgtcgtca gcctgcgtcc gatggcctcg tcgacggctc aggcccccgc gacggcgccg     180
ccgggtctga aggagggcat cgcggggctg tacgacgagt cgtcgggget gtgggagaac     240
atctggggcg accacatgca ccacggcttc tacgactcga gcgaggccgc ctccatggcc     300
gatcaccgcc gcgcccagat ccgcatgatc gaggaggcgc tcgccttcgc cggtgtccca     360
gcctcagatg atccagagaa gacaccaaaa acaatagtcg atgtcggatg tggcattggt     420
ggtagctcaa ggtacttggc gaagaaatac ggancgcagt gcactgggat cacgttgagc     480
cctgttcaag ccgagagagg aaatgctctc gctgcagcgc aggggttgtc ggatcaggtt     540
actctgcaag ttgctgatgc tctggagcaa ccgtttcctg acgggcagtt cgatctggtg     600
tggtccatgg agagtggcga gcacatgccg acaagagaa agtttgttag tgagctagca     660
cgcgtggcgg ctcctggagg acaataatc atcgtgacat ggtgccatag gaacctggat     720
ccatccgaaa cctcgctaaa gcccgatgaa ctgagcctcc tgaggaggat atgcgacgcg     780
tactacctcc cggactggtg ctcaccttca gactatgtga acattgccaa gtcactgtct     840
ctcgaggata tcaagacagc tgactggtcg gagaacgtgg cccgttttg gcccgccgtg     900
ataaaatcag cgctaacatg gaagggcttc acctctctgc tgacgaccgg atggaagacg     960
atcagaggcg cgatggtgat gccgctaatg atccagggct acaagaaggg gctcatcaaa    1020
ttcaccatca tcacctgtcg caagcctgga gccgcgtagt gatctatacc gnccacggcg    1080
tcnttaactc tnacggaaan ct                                              1102

<210> SEQ ID NO 22
<211> LENGTH: 352
<212> TYPE: PRT
<213> ORGANISM: Zea mays
<220> FEATURE:
<221> NAME/KEY: UNSURE
<222> LOCATION: (152)
<223> OTHER INFORMATION: Xaa = ANY AMINO ACID

<400> SEQUENCE: 22

Met Ala His Ala Ala Leu Leu His Cys Ser Gln Ser Ser Arg Ser Leu
  1               5                  10                  15

Ala Ala Cys Arg Arg Gly Ser His Tyr Arg Ala Pro Ser His Val Pro
             20                  25                  30

Arg His Ser Arg Arg Leu Arg Arg Ala Val Val Ser Leu Arg Pro Met
         35                  40                  45

Ala Ser Ser Thr Ala Gln Ala Pro Ala Thr Ala Pro Pro Gly Leu Lys
     50                  55                  60

Glu Gly Ile Ala Gly Leu Tyr Asp Glu Ser Ser Gly Leu Trp Glu Asn
 65                  70                  75                  80

Ile Trp Gly Asp His Met His His Gly Phe Tyr Asp Ser Ser Glu Ala
```

```
                    85                  90                  95
Ala Ser Met Ala Asp His Arg Arg Ala Gln Ile Arg Met Ile Glu Glu
                100                 105                 110
Ala Leu Ala Phe Ala Gly Val Pro Ala Ser Asp Asp Pro Glu Lys Thr
            115                 120                 125
Pro Lys Thr Ile Val Asp Val Gly Cys Gly Ile Gly Gly Ser Ser Arg
        130                 135                 140
Tyr Leu Ala Lys Lys Tyr Gly Xaa Gln Cys Thr Gly Ile Thr Leu Ser
145                 150                 155                 160
Pro Val Gln Ala Glu Arg Gly Asn Ala Leu Ala Ala Gln Gly Leu
                165                 170                 175
Ser Asp Gln Val Thr Leu Gln Val Ala Asp Ala Leu Glu Gln Pro Phe
            180                 185                 190
Pro Asp Gly Gln Phe Asp Leu Val Trp Ser Met Glu Ser Gly Glu His
        195                 200                 205
Met Pro Asp Lys Arg Lys Phe Val Ser Glu Leu Ala Arg Val Ala Ala
    210                 215                 220
Pro Gly Gly Thr Ile Ile Ile Val Thr Trp Cys His Arg Asn Leu Asp
225                 230                 235                 240
Pro Ser Glu Thr Ser Leu Lys Pro Asp Glu Leu Ser Leu Leu Arg Arg
                245                 250                 255
Ile Cys Asp Ala Tyr Tyr Leu Pro Asp Trp Cys Ser Pro Ser Asp Tyr
            260                 265                 270
Val Asn Ile Ala Lys Ser Leu Ser Leu Glu Asp Ile Lys Thr Ala Asp
        275                 280                 285
Trp Ser Glu Asn Val Ala Pro Phe Trp Pro Ala Val Ile Lys Ser Ala
    290                 295                 300
Leu Thr Trp Lys Gly Phe Thr Ser Leu Leu Thr Thr Gly Trp Lys Thr
305                 310                 315                 320
Ile Arg Gly Ala Met Val Met Pro Leu Met Ile Gln Gly Tyr Lys Lys
                325                 330                 335
Gly Leu Ile Lys Phe Thr Ile Ile Thr Cys Arg Lys Pro Gly Ala Ala
            340                 345                 350

<210> SEQ ID NO 23
<211> LENGTH: 521
<212> TYPE: DNA
<213> ORGANISM: Oryza sativa
<220> FEATURE:
<221> NAME/KEY: unsure
<222> LOCATION: (269)
<223> OTHER INFORMATION: n = a, c, g, or t
<220> FEATURE:
<221> NAME/KEY: unsure
<222> LOCATION: (274)
<223> OTHER INFORMATION: n = a, c, g, or t
<220> FEATURE:
<221> NAME/KEY: unsure
<222> LOCATION: (286)
<223> OTHER INFORMATION: n = a, c, g, or t
<220> FEATURE:
<221> NAME/KEY: unsure
<222> LOCATION: (302)
<223> OTHER INFORMATION: n = a, c, g, or t
<220> FEATURE:
<221> NAME/KEY: unsure
<222> LOCATION: (330)
<223> OTHER INFORMATION: n = a, c, g, or t
<220> FEATURE:
<221> NAME/KEY: unsure
<222> LOCATION: (381)..(382)
<223> OTHER INFORMATION: n = a, c, g, or t
```

```
<220> FEATURE:
<221> NAME/KEY: unsure
<222> LOCATION: (387)
<223> OTHER INFORMATION: n = a, c, g, or t
<220> FEATURE:
<221> NAME/KEY: unsure
<222> LOCATION: (398)
<223> OTHER INFORMATION: n = a, c, g, or t
<220> FEATURE:
<221> NAME/KEY: unsure
<222> LOCATION: (418)
<223> OTHER INFORMATION: n = a, c, g, or t
<220> FEATURE:
<221> NAME/KEY: unsure
<222> LOCATION: (429)
<223> OTHER INFORMATION: n = a, c, g, or t
<220> FEATURE:
<221> NAME/KEY: unsure
<222> LOCATION: (436)
<223> OTHER INFORMATION: n = a, c, g, or t
<220> FEATURE:
<221> NAME/KEY: unsure
<222> LOCATION: (462)
<223> OTHER INFORMATION: n = a, c, g, or t
<220> FEATURE:
<221> NAME/KEY: unsure
<222> LOCATION: (467)
<223> OTHER INFORMATION: n = a, c, g, or t
<220> FEATURE:
<221> NAME/KEY: unsure
<222> LOCATION: (473)
<223> OTHER INFORMATION: n = a, c, g, or t
<220> FEATURE:
<221> NAME/KEY: unsure
<222> LOCATION: (514)
<223> OTHER INFORMATION: n = a, c, g, or t

<400> SEQUENCE: 23
cttacagaca aacggcagtt tgtaagcgag ctggcacgcg tcgcagctcc tggggcgaga      60
ataatcattg tgacctggtg ccataggaac ctcgagccat ccgaagagtc cctgaaacct    120
gatgagctga atctcctgaa aaggatatgc gatgcatatt atctcccaga ctggtgctct    180
ccttctgatt atgtcaaaat tgccgagtca ctgtctcttg aggatataag gacagctgat    240
tggtcaagag aacgtcgccc caatccggnc tgcnggttat taaataagc aattgacatg    300 gnaagggtta actttctcct ggctaagaan tgggtgggaa gacgattaag aaggtggaat    360
gggtgatgcc tccggatgat nnaaggntac aaagaaangg gtcaacaaat ttaacaanaa    420
caacctgtnc caaagncccg aaacaacgca ataataccc antaatnaaa ttncgctcct    480
ggctaacctt ctccaacaac gaattaatgg aaanttctga c                         521

<210> SEQ ID NO 24
<211> LENGTH: 172
<212> TYPE: PRT
<213> ORGANISM: Oryza sativa

<400> SEQUENCE: 24

Phe Arg His Gly His Ala Leu Ala Gln Pro Phe Pro Asp Gly Gln Phe
 1               5                  10                  15

Asp Leu Val Trp Ser Met Glu Ser Asp Glu His Met Pro Asp Lys Arg
            20                  25                  30

Gln Phe Val Ser Glu Leu Ala Arg Val Ala Ala Pro Gly Ala Arg Ile
        35                  40                  45

Ile Ile Val Thr Trp Cys His Arg Asn Leu Glu Pro Ser Glu Glu Ser
    50                  55                  60

Leu Lys Pro Asp Glu Leu Asn Leu Leu Lys Arg Ile Cys Asp Ala Tyr
65                  70                  75                  80
```

Tyr Leu Pro Asp Trp Cys Ser Pro Ser Asp Tyr Val Lys Ile Ala Glu
            85                  90                  95

Ser Leu Ser Leu Glu Asp Ile Arg Thr Ala Asp Trp Ser Glu Asn Val
            100                 105                 110

Ala Pro Phe Trp Pro Ala Val Ile Lys Ser Ala Leu Thr Trp Lys Gly
            115                 120                 125

Leu Thr Ser Leu Leu Arg Ser Gly Trp Glu Thr Val Arg Gly Ala Met
            130                 135                 140

Val Met Pro Leu Val Ile Glu Gly Tyr Lys Lys Gly Leu Ile Lys Phe
145                 150                 155                 160

Pro Ile Ile Thr Cys Arg Lys Pro Glu Thr Thr Gln
                165                 170

<210> SEQ ID NO 25
<211> LENGTH: 464
<212> TYPE: DNA
<213> ORGANISM: Oryza sativa

<400> SEQUENCE: 25
gcacgagtac agcccacggg cgcactggca ccgctgcatc cactgctccg ctgcacgagc     60
cgtcatctct gcgcctcggc ttcccctcgc gccggcctct gcctccacca ccaccgccgc    120
cgccgccgca gcagccggag gacgaaactc gccgtgcgcg cgatggcacc gacgttgtcc    180
tcgtcgtcga cggcggcggc agctcccccg gggctgaagg agggcatcgc ggggctctac    240
gacgagtcgt ccggcgtgtg ggagagcatc tgggcgagc acatgcacca cggcttctac    300
gacgccggcg aggccgcctc catgtccgac caccgccgcg cccagatccg catgatcgag    360
gaatccctcg ccttcgccgc cgttccccga tgatgcggga aacaaaccca aaagtgttat    420
ttactgtttg gtgttgcaaa tgggggtacc tccaaaaaac tttg                     464

<210> SEQ ID NO 26
<211> LENGTH: 128
<212> TYPE: PRT
<213> ORGANISM: Oryza sativa

<400> SEQUENCE: 26

Ala Arg Val Gln Pro Thr Gly Ala Leu Ala Pro Leu His Pro Leu Leu
1               5                   10                  15

Arg Cys Thr Ser Arg His Leu Cys Ala Ser Ala Ser Pro Arg Ala Gly
            20                  25                  30

Leu Cys Leu His His Arg Arg Arg Arg Ser Arg Arg Thr
            35                  40                  45

Lys Leu Ala Val Arg Ala Met Ala Pro Thr Leu Ser Ser Ser Ser Thr
    50                  55                  60

Ala Ala Ala Ala Pro Pro Gly Leu Lys Glu Gly Ile Ala Gly Leu Tyr
65                  70                  75                  80

Asp Glu Ser Ser Gly Val Trp Glu Ser Ile Trp Gly Glu His Met His
            85                  90                  95

His Gly Phe Tyr Asp Ala Gly Glu Ala Ala Ser Met Ser Asp His Arg
            100                 105                 110

Arg Ala Gln Ile Arg Met Ile Glu Glu Ser Leu Ala Phe Ala Ala Val
            115                 120                 125

<210> SEQ ID NO 27
<211> LENGTH: 1189
<212> TYPE: DNA

<213> ORGANISM: Glycine max

<400> SEQUENCE: 27

```
ggacatggcc accgtggtga ggatcccaac aatctcatgc atccacatcc acacgttccg      60
ttcccaatcc cctcgcactt tcgccagaat ccgggtcgga cccaggtcgt gggctcctat     120
tcgggcatcg gcagcgagct cggagagagg ggagatagta ttggagcaga agccgaagaa     180
ggatgacaag aagaagctgc agaagggaat cgcagagttt tacgacgagt cgtctggctt     240
atgggagaac atttggggcg accacatgca ccatggcttt tatgactcgg attccactgt     300
ttcgctttcg gatcatcgtg ctgctcagat ccgaatgatc caagagtctc ttcgctttgc     360
ctctgtttct gaggagcgta gtaaatggcc caagagtata gttgatgttg gtgtgtggcat     420
aggtggcagc tctagatacc tggccaagaa atttggagca accagtgtag gcatcactct     480
gagtcctgtt caagctcaaa gagcaaatgc tcttgctgct gctcaaggat tggctgataa     540
ggtttccttt caggttgctg acgctctaca gcaaccattc tctgacggcc agtttgatct     600
ggtgtggtcc atggagagtg gagagcatat gcctgacaaa gctaagtttg ttggagagtt     660
agctcgggta gcagcaccag gtgccattat aataatagta acatggtgcc acagggatct     720
tggccctgac gaacaatcct tacatccatg ggagcaagat ctcttaaaga agatttgcga     780
tgcatattac ctccctgcct ggtgctcaac ttctgattat gttaagttgc tccaatccct     840
gtcacttcag gacatcaagt cagaagattg gtctcgcttt gttgctccat tttggccagc     900
agtgatacgc tcagccttca catggaaggg tctatcttca ctcttgagca gtggacaaaa     960
aacgataaaa ggagctttgg ctatgccatt gatgatagag ggatacaaga agatctaat    1020
taagtttgcc atcattacat gtcgaaaacc tgaataaatg gagaggcagg attactttta   1080
tagaatgaac caagtttcca acaggtcgtt tatttcgata gttgagaaac aagagaaaaa    1140
ataaatgaaa ggggttgttc gattttaaaa aaaaaaaaaa aaaaaaaa                 1189
```

<210> SEQ ID NO 28
<211> LENGTH: 350
<212> TYPE: PRT
<213> ORGANISM: Glycine max

<400> SEQUENCE: 28

```
Met Ala Thr Val Val Arg Ile Pro Thr Ile Ser Cys Ile His Ile His
  1               5                  10                  15

Thr Phe Arg Ser Gln Ser Pro Arg Thr Phe Ala Arg Ile Arg Val Gly
                 20                  25                  30

Pro Arg Ser Trp Ala Pro Ile Arg Ala Ser Ala Ala Ser Ser Glu Arg
             35                  40                  45

Gly Glu Ile Val Leu Glu Gln Lys Pro Lys Lys Asp Lys Lys Lys
     50                  55                  60

Leu Gln Lys Gly Ile Ala Glu Phe Tyr Asp Glu Ser Ser Gly Leu Trp
 65                  70                  75                  80

Glu Asn Ile Trp Gly Asp His Met His His Gly Phe Tyr Asp Ser Asp
                 85                  90                  95

Ser Thr Val Ser Leu Ser Asp His Arg Ala Ala Gln Ile Arg Met Ile
                100                 105                 110

Gln Glu Ser Leu Arg Phe Ala Ser Val Ser Glu Glu Arg Ser Lys Trp
            115                 120                 125

Pro Lys Ser Ile Val Asp Val Gly Cys Gly Ile Gly Gly Ser Ser Arg
        130                 135                 140
```

-continued

```
Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Gln Gly Leu
            165                 170                 175

Ala Asp Lys Val Ser Phe Gln Val Ala Asp Ala Leu Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
            245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
            275                 280                 285

Trp Ser Arg Phe Val Ala Pro Phe Trp Pro Ala Val Ile Arg Ser Ala
    290                 295                 300

Phe Thr Trp Lys Gly Leu Ser Ser Leu Leu Ser Ser Gly Gln Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
            340                 345                 350
```

```
<210> SEQ ID NO 29
<211> LENGTH: 1257
<212> TYPE: DNA
<213> ORGANISM: Triticum aestivum
<220> FEATURE:
<221> NAME/KEY: unsure
<222> LOCATION: (31)
<223> OTHER INFORMATION: n = a, c, g, or t
<220> FEATURE:
<221> NAME/KEY: unsure
<222> LOCATION: (151)
<223> OTHER INFORMATION: n = a, c, g, or t

<400> SEQUENCE: 29
gaggctccaa atacaaaatg gcaaactccg nccgccctgc tccactcact cctctccacc      60
gcctggacgc cgcgccgccg cctcgaccga gcctcggcca cgcggctcgc ccgtccccc     120
ggcctgtcct gccgctcctc ccggccagac ngctccgtgc gcccgatggc gtcgtcgacg     180
accgcggccc gggcgacgcg cgccgccgg ggctgaagga gggcatcgcg gggctctacg     240
acgagtcgtc cggcctgtgg gagagcatct ggggcgagca catgcaccac ggcttctacg     300
actccggcga ggccgcctcc atgtccgacc accgccgcgc ccagatccgc atgatcgagg     360
aggccctcgc cttcgccgcc gtccccgacg atccgacaaa caaacccaaa acgattgttg     420
atgttggatg cggaatcggt ggtagctcaa gatacctggc gaacaaatat ggagcacaat     480
gctctgggat cacattgagc ccagtgcaag ctgagagagg aaatgccctc gcggcagcgc     540
aggggttgtc ggacaaggct tctttccaag ttgctgatgc tctggagcaa ccatttcctg     600
atgggcagtt tgatcttgtc tggtctatgg agagtggtga gcacatgccg aacaaacaga     660
agtttgtaag cgagctggca cgcgtcgcag ctccaggagc aactatcatc atcgtgacct     720
```

```
ggtgccatag gaacctcgcg ccgtcggagg actcactgaa acctgacgag ctgaatcttt    780
tgaaaaagat ttgtgatgca tattacctcc cggattggtg ctcgccctcg gattatgtca    840
agattgccga gtcattgtct cttgaggata tcaaaacggc cgactggtca gaaaacgtgg    900
ccccgttctg gcctgctgtc atccaatcag cactgacatg gaaaggcctc acttctctac    960
taaggagtgg atggaagacg ataaagggag cactggtgat gcctctcatg atccaaggct   1020
acaagaaagg cctcattaag ttcagcatca tcacctgccg caaaccccaa gcagccatag   1080
aaggagaacc tgaggccgca tcgcccagtg tagaatagaa cccatgtgat tggaatagac   1140
tcggcttgct gtcgcctcgt agctgaataa ttttgtgtta ccgtgcctct ctatctgcaa   1200
ctggaagtgg cataggaaag tggttcctaa agcaaaaaaa aaaaaaaaaa aaaaaaa      1257
```

<210> SEQ ID NO 30
<211> LENGTH: 366
<212> TYPE: PRT
<213> ORGANISM: Triticum aestivum
<220> FEATURE:
<221> NAME/KEY: UNSURE
<222> LOCATION: (5)
<223> OTHER INFORMATION: Xaa = ANY AMINO ACID
<220> FEATURE:
<221> NAME/KEY: UNSURE
<222> LOCATION: (45)
<223> OTHER INFORMATION: Xaa = ANY AMINO ACID

<400> SEQUENCE: 30

```
Met Ala Asn Ser Xaa Arg Pro Ala Pro Leu Thr Pro Leu His Arg Leu
  1               5                  10                  15

Asp Ala Ala Pro Pro Arg Pro Ser Leu Gly His Ala Ala Arg Pro
             20                  25                  30

Val Pro Arg Pro Val Leu Pro Leu Pro Ala Arg Xaa Leu Arg Ala
         35                  40                  45

Pro Asp Gly Val Val Asp Arg Gly Pro Gly Asp Ala Ala Pro Pro
     50                  55                  60

Gly Leu Lys Glu Gly Ile Ala Gly Leu Tyr Asp Glu Ser Ser Gly Leu
 65                  70                  75                  80

Trp Glu Ser Ile Trp Gly Glu His Met His His Gly Phe Tyr Asp Ser
                 85                  90                  95

Gly Glu Ala Ala Ser Met Ser Asp His Arg Arg Ala Gln Ile Arg Met
            100                 105                 110

Ile Glu Glu Ala Leu Ala Phe Ala Ala Val Pro Asp Asp Pro Thr Asn
        115                 120                 125

Lys Pro Lys Thr Ile Val Asp Val Gly Cys Gly Ile Gly Gly Ser Ser
130                 135                 140

Arg Tyr Leu Ala Asn Lys Tyr Gly Ala Gln Cys Ser Gly Ile Thr Leu
145                 150                 155                 160

Ser Pro Val Gln Ala Glu Arg Gly Asn Ala Leu Ala Ala Ala Gln Gly
                165                 170                 175

Leu Ser Asp Lys Ala Ser Phe Gln Val Ala Asp Ala Leu Glu Gln Pro
            180                 185                 190

Phe Pro Asp Gly Gln Phe Asp Leu Val Trp Ser Met Glu Ser Gly Glu
        195                 200                 205

His Met Pro Asn Lys Gln Lys Phe Val Ser Glu Leu Ala Arg Val Ala
    210                 215                 220

Ala Pro Gly Ala Thr Ile Ile Ile Val Thr Trp Cys His Arg Asn Leu
225                 230                 235                 240
```

```
Ala Pro Ser Glu Asp Ser Leu Lys Pro Asp Glu Leu Asn Leu Leu Lys
            245                 250                 255

Lys Ile Cys Asp Ala Tyr Tyr Leu Pro Asp Trp Cys Ser Pro Ser Asp
            260                 265                 270

Tyr Val Lys Ile Ala Glu Ser Leu Ser Leu Glu Asp Ile Lys Thr Ala
            275                 280                 285

Asp Trp Ser Glu Asn Val Ala Pro Phe Trp Pro Ala Val Ile Gln Ser
            290                 295                 300

Ala Leu Thr Trp Lys Gly Leu Thr Ser Leu Leu Arg Ser Gly Trp Lys
305                 310                 315                 320

Thr Ile Lys Gly Ala Leu Val Met Pro Leu Met Ile Gln Gly Tyr Lys
            325                 330                 335

Lys Gly Leu Ile Lys Phe Ser Ile Ile Thr Cys Arg Lys Pro Gln Ala
            340                 345                 350

Ala Ile Glu Gly Glu Pro Glu Ala Ala Ser Pro Ser Val Glu
            355                 360                 365

<210> SEQ ID NO 31
<211> LENGTH: 1605
<212> TYPE: DNA
<213> ORGANISM: Catalpa sp.

<400> SEQUENCE: 31
gcacgaggca ccacttcacc accaccacca ccaccaccac caccacaact gcttccaccg      60
ccgcagagtc actctatcag ttaagatcaa agcaacaagt tcagaatccc aaacaatggg     120
caagcagacg accacttccg ccaccgccgc ggacgggtcc aaagatgcgc atgcagaatt     180
caagctggtg ggcttcaaga atttcgtcag gaccaacccc aagtccgacc acttctgcgt     240
ccaccgcttc caccatatag agttctggtg cggcgacgcc accaacaccg ccaagcgctt     300 ctcttgggc ctcggtatgc ccctcgtcgc caaatcggat cttccactg gaaactccgc       360 tcatgcctcg tatcttcttc ggtctggcga actcaacttc ctcttcacga gcccttactc     420
tccttcaatc tccgccccct cctccgccgc catccccagt ttctccttct ccacctacca     480 gtctttacc tcctcccatg gcctcgctgt tcgtgcggtg gctattcagg tcgattcggc      540
cttttcggct tactctgcct ccatttcccg cggcgccaaa cccgtgtccg caccgattct     600
tttatctgac aacaagactg ccattgcgga ggttcattta tatggagact cagtgttgcg     660
attcgtgagc tatggtgata tgggacagg cccagatgga tggttcttgc gggctttga      720 gcctgtggat gatcagatgt cttataaaga attggattat gggattagaa ggctagatca     780
tgctgtagga aatgtgcccg aactcggtcc agttgtggat tacttgaaaa aattcacagg     840
gtttcatgaa tttgcagagt ttacttcaga ggatgtggga acagcagaaa gtggattgaa     900
ttctatggtt ttagcgaaca caatgaaaa tgtgttgtta cctctgaacg aaccggtgtt      960
tgggaccaag aggaagagcc agattcagac ttatttggag cacaatgaag gccaggtgt     1020 acagcatttg gcattagtga gtgaggatat ctttaacaca ttaagggaaa tgagaaagag     1080
gagtggagtt gggggattcg agttcatgcc ttcgcctccg cttacttatt acaagaatct     1140
caagaacaga gctggagatg tgctgaggga tgagcagatt gaggagtgtg agaagttggg     1200
gatcttggtg gacagggatg atcagggggac tttgcttcag atttttcacca gcctgtggg     1260 tgataggcca acgctattca tagagatcat tcagagaatc gggtgcatgc tcaaagacga     1320
acaaggaaag ctctaccaga agagtggttg tggaggattt ggaaagggca acttctccga     1380
actcttcaaa tccatcgaag aatacgagaa aatgctcgaa gcaaagcaag tcactgaaac     1440
```

```
agcgtcggcc tgagttctga gtccttccta ctgtgttgta gatatgttga tgaaccaatg   1500
tcctgtcggg acataggttg ttcttatgct gtactaaact gtagttgaca agaagtttta   1560
cttaataata tatcgtactt tctataaaaa aaaaaaaaa aaaaa                    1605
```

<210> SEQ ID NO 32
<211> LENGTH: 445
<212> TYPE: PRT
<213> ORGANISM: Catalpa sp.

<400> SEQUENCE: 32

```
Met Gly Lys Gln Thr Thr Ser Ala Thr Ala Ala Asp Gly Ser Lys
 1               5                  10                  15

Asp Ala His Ala Glu Phe Lys Leu Val Gly Phe Lys Asn Phe Val Arg
            20                  25                  30

Thr Asn Pro Lys Ser Asp His Phe Cys Val His Arg Phe His His Ile
        35                  40                  45

Glu Phe Trp Cys Gly Asp Ala Thr Asn Thr Ala Lys Arg Phe Ser Trp
    50                  55                  60

Gly Leu Gly Met Pro Leu Val Ala Lys Ser Asp Leu Ser Thr Gly Asn
65                  70                  75                  80

Ser Ala His Ala Ser Tyr Leu Leu Arg Ser Gly Glu Leu Asn Phe Leu
                85                  90                  95

Phe Thr Ser Pro Tyr Ser Pro Ser Ile Ser Ala Pro Ser Ser Ala Ala
            100                 105                 110

Ile Pro Ser Phe Ser Phe Ser Thr Tyr Gln Ser Phe Thr Ser Ser His
        115                 120                 125

Gly Leu Ala Val Arg Ala Val Ala Ile Gln Val Asp Ser Ala Phe Ser
    130                 135                 140

Ala Tyr Ser Ala Ser Ile Ser Arg Gly Ala Lys Pro Val Ser Ala Pro
145                 150                 155                 160

Ile Leu Leu Ser Asp Asn Lys Thr Ala Ile Ala Glu Val His Leu Tyr
                165                 170                 175

Gly Asp Ser Val Leu Arg Phe Val Ser Tyr Gly Asp Asn Gly Thr Gly
            180                 185                 190

Pro Asp Gly Trp Phe Leu Pro Gly Phe Glu Pro Val Asp Asp Gln Met
        195                 200                 205

Ser Tyr Lys Glu Leu Asp Tyr Gly Ile Arg Arg Leu Asp His Ala Val
    210                 215                 220

Gly Asn Val Pro Glu Leu Gly Pro Val Val Asp Tyr Leu Lys Lys Phe
225                 230                 235                 240

Thr Gly Phe His Glu Phe Ala Glu Phe Thr Ser Glu Asp Val Gly Thr
                245                 250                 255

Ala Glu Ser Gly Leu Asn Ser Met Val Leu Ala Asn Asn Asn Glu Asn
            260                 265                 270

Val Leu Leu Pro Leu Asn Glu Pro Val Phe Gly Thr Lys Arg Lys Ser
        275                 280                 285

Gln Ile Gln Thr Tyr Leu Glu His Asn Glu Gly Pro Gly Val Gln His
    290                 295                 300

Leu Ala Leu Val Ser Glu Asp Ile Phe Asn Thr Leu Arg Glu Met Arg
305                 310                 315                 320

Lys Arg Ser Gly Val Gly Gly Phe Glu Phe Met Pro Ser Pro Pro Leu
                325                 330                 335

Thr Tyr Tyr Lys Asn Leu Lys Asn Arg Ala Gly Asp Val Leu Arg Asp
```

```
                340                 345                 350
Glu Gln Ile Glu Glu Cys Glu Lys Leu Gly Ile Leu Val Asp Arg Asp
                355                 360                 365

Asp Gln Gly Thr Leu Leu Gln Ile Phe Thr Lys Pro Val Gly Asp Arg
            370                 375                 380

Pro Thr Leu Phe Ile Glu Ile Ile Gln Arg Ile Gly Cys Met Leu Lys
385                 390                 395                 400

Asp Glu Gln Gly Lys Leu Tyr Gln Lys Ser Gly Cys Gly Gly Phe Gly
                405                 410                 415

Lys Gly Asn Phe Ser Glu Leu Phe Lys Ser Ile Glu Glu Tyr Glu Lys
                420                 425                 430

Met Leu Glu Ala Lys Gln Val Thr Glu Thr Ala Ser Ala
                435                 440                 445

<210> SEQ ID NO 33
<211> LENGTH: 1106
<212> TYPE: DNA
<213> ORGANISM: Oryza sativa

<400> SEQUENCE: 33
gcacgaggaa gagctacggc ctccgccggt tcgaccacgt cgtcggcaac gtgccggagc      60
tcgctccggt agccgcgtac atctccgggt tcaccgggtt ccacgagttc gccgagttca     120
ccgccgagga cgtgggcacc gccgagagcg gcctcaactc ggtggtgctc gccaacaacg     180
cggagaccgt gctgctgccg ctcaacgagc cggtgcacgg caccaagcgg cggagccaga     240
tacagacgta cctggaccac cacggcggcc cgggggtgca gcacatcgcg ctggccagcg     300
acgacgtgct cgggacgctg agggagatgc gggcgcgctc cgccatgggc ggcttcgagt     360
tcttggcgcc gccgccgccc aactactacg acggcgtgcg gcggcgcgcc ggggacgtgc     420
tctcggagga gcagatcaac gagtgccagg agctcgggt gctcgtggac agggatgacc     480
aggggtgtt gctccagatc ttcaccaagc cagtaggaga caggccaacc tttttcttgg     540
agatgataca aaggattggg tgcatggaga aggatgagag tgggcaggag taccagaagg     600
gcggctgcgg cgggtttggg aagggcaact tctcggagct gttcaagtcc attgaggagt     660
atgagaaatc ccttgaagcc aagcaagccc ctacagttca aggatcctag gtaggaactg     720
gaggcctgga gcaacagatg taaccagtgt atttgtatta tggagcagaa gaaaaaagat     780
gtgctttcac tgctttgtga tatgtgtcat gcaagttgat gttgtaattt gtggaagctg     840
aagacaaatg atggtacaat cactgtaata gataatagac atggatcaca tacaagaatg     900
taacctagtg ttggcattgc tgctgtacaa tcttgcttgg aaataaaata ataatcaacc     960
tggagaaaga atgtaaccta ctgttggcat tgctgatgta caatcttttt ttggaaataa    1020
aataagaatc cccccaaaa aaaaaaaaaa aaaaaaaaa aaaaaaaaa aaaaaaaaa         1080
aaaaaaaaaa aaaaaaaaaa aaaaaa                                         1106

<210> SEQ ID NO 34
<211> LENGTH: 235
<212> TYPE: PRT
<213> ORGANISM: Oryza sativa

<400> SEQUENCE: 34

Thr Arg Lys Ser Tyr Gly Leu Arg Arg Phe Asp His Val Val Gly Asn
1               5                   10                  15

Val Pro Glu Leu Ala Pro Val Ala Ala Tyr Ile Ser Gly Phe Thr Gly
                20                  25                  30
```

```
Phe His Glu Phe Ala Glu Phe Thr Ala Glu Asp Val Gly Thr Ala Glu
             35                  40                  45

Ser Gly Leu Asn Ser Val Val Leu Ala Asn Asn Ala Glu Thr Val Leu
 50                  55                  60

Leu Pro Leu Asn Glu Pro Val His Gly Thr Lys Arg Arg Ser Gln Ile
 65                  70                  75                  80

Gln Thr Tyr Leu Asp His His Gly Gly Pro Gly Val Gln His Ile Ala
                 85                  90                  95

Leu Ala Ser Asp Asp Val Leu Gly Thr Leu Arg Glu Met Arg Ala Arg
                100                 105                 110

Ser Ala Met Gly Gly Phe Glu Phe Leu Ala Pro Pro Pro Asn Tyr
                115                 120                 125

Tyr Asp Gly Val Arg Arg Ala Gly Asp Val Leu Ser Glu Glu Gln
                130                 135                 140

Ile Asn Glu Cys Gln Glu Leu Gly Val Leu Val Asp Arg Asp Gln
145                 150                 155                 160

Gly Val Leu Leu Gln Ile Phe Thr Lys Pro Val Gly Asp Arg Pro Thr
                165                 170                 175

Phe Phe Leu Glu Met Ile Gln Arg Ile Gly Cys Met Glu Lys Asp Glu
                180                 185                 190

Ser Gly Gln Glu Tyr Gln Lys Gly Gly Cys Gly Phe Gly Lys Gly
                195                 200                 205

Asn Phe Ser Glu Leu Phe Lys Ser Ile Glu Glu Tyr Glu Lys Ser Leu
210                 215                 220

Glu Ala Lys Gln Ala Pro Thr Val Gln Gly Ser
225                 230                 235

<210> SEQ ID NO 35
<211> LENGTH: 1550
<212> TYPE: DNA
<213> ORGANISM: Glycine max

<400> SEQUENCE: 35
tcacaccaca ccaatgccaa tacccatgtg caacgaaatt caagcccaag cccaagccca      60
agcccaagcc caacctgggt ttaagctcgt cggtttcaaa aacttcgtcc gaaccaatcc     120
taagtcggac cgcttcaag tcaaccgctt ccaccacatc gagttctggt gcaccgatgc     180
caccaacgcc tctcgccgat ctcttgggg acttggaatg cctattgtgg caaaatctga     240
tctctccacc ggaaaccaaa tccacgcctc ctacctcctc cgctcggcg acctctcctt     300 cctcttctcc gctccttact ctccctctct ctccgccggc tcctccgctg cctcctccgc     360
ctccattccc agtttcgacg ccgccacctg ccttgccttc gctgccaaac acggcttcgg     420
cgtccgcgcc atcgccttgg aagtcgccga cgcggaagcc gctttcagcg ccagcgtcgc     480
gaaaggagcc gagccggcgt cgccgccggt tctcgtcgac gatcgcaccg gcttcgcgga     540
ggtgcgcctc tacggcgacg tggtgctccg ctacgtcagc tacaaggacg ccgcgccgca     600
ggcgccacac gcagatccgt cgcggtggtt cctgccggga ttcgaggccg gcgtcgtc      660 gtcttcgttt ccggagctgg actacgggat ccggcggctg gaccacgccg tcgggaacgt     720
tccggagctg cgccggcgg tgaggtacct gaaaggcttc agcggattcc acgagttcgc     780
ggagttcacc gcggaggacg tgggaacgag cgagagcggg ttgaactcgg tggttctggc     840
gaacaactcg gagacggtgt tgctgccgct gaacgagccg gttacgaa cgaagaggaa      900 gagccagatt gagacgtatt tggaacacaa cgaaggtgct ggtgtgcagc accttgcgct     960
```

-continued

```
tgttactcac gacatcttca ccacactgag agagatgaga aagcgaagtt tccttggtgg    1020
atttgagttc atgccttctc ctcctcccac ctattacgcc aacctccaca accgtgccgc    1080
tgatgtgttg accgttgacc agattaagca gtgtgaggag cttgggattc ttgttgacag    1140
agatgatcag ggcactctgc ttcagatttt caccaagcct gttggggaca ggccaacgat    1200
attcatagag ataattcaga ggatcgggtg catggtggag gatgaggaag gaaggtgta     1260 ccagaagggt gcatgtgggg gttttgggaa aggcaatttt tctgagcttt tcaaatccat    1320
tgaagaatat gagaagactt tggaagctaa aagaaccgcg taagcacatt ggaagaacac    1380
aaatactcct ttgttgaaat gattaatgag gaatcaatgt ggcatagggt gtttatactc    1440
tataatacat agaattacaa tgatagtgtc ctcccttgta tgaaaatgaa atcacagaaa    1500
cttttatgga tagtattttt ctattaaaaa aaaaaaaaa aaaaaaaaa                 1550
```

<210> SEQ ID NO 36
<211> LENGTH: 449
<212> TYPE: PRT
<213> ORGANISM: Glycine max

<400> SEQUENCE: 36

```
Met Pro Ile Pro Met Cys Asn Glu Ile Gln Ala Gln Ala Gln Ala Gln
  1               5                  10                  15

Ala Gln Ala Gln Pro Gly Phe Lys Leu Val Gly Phe Lys Asn Phe Val
                 20                  25                  30

Arg Thr Asn Pro Lys Ser Asp Arg Phe Gln Val Asn Arg Phe His His
             35                  40                  45

Ile Glu Phe Trp Cys Thr Asp Ala Thr Asn Ala Ser Arg Arg Phe Ser
         50                  55                  60

Trp Gly Leu Gly Met Pro Ile Val Ala Lys Ser Asp Leu Ser Thr Gly
     65                  70                  75                  80

Asn Gln Ile His Ala Ser Tyr Leu Leu Arg Ser Gly Asp Leu Ser Phe
                     85                  90                  95

Leu Phe Ser Ala Pro Tyr Ser Pro Ser Leu Ser Ala Gly Ser Ser Ala
                100                 105                 110

Ala Ser Ser Ala Ser Ile Pro Ser Phe Asp Ala Ala Thr Cys Leu Ala
            115                 120                 125

Phe Ala Ala Lys His Gly Phe Gly Val Arg Ala Ile Ala Leu Glu Val
        130                 135                 140

Ala Asp Ala Glu Ala Ala Phe Ser Ala Ser Val Ala Lys Gly Ala Glu
145                 150                 155                 160

Pro Ala Ser Pro Pro Val Leu Val Asp Asp Arg Thr Gly Phe Ala Glu
                165                 170                 175

Val Arg Leu Tyr Gly Asp Val Val Leu Arg Tyr Val Ser Tyr Lys Asp
            180                 185                 190

Ala Ala Pro Gln Ala Pro His Ala Asp Pro Ser Arg Trp Phe Leu Pro
        195                 200                 205

Gly Phe Glu Ala Ala Ala Ser Ser Ser Phe Pro Glu Leu Asp Tyr
    210                 215                 220

Gly Ile Arg Arg Leu Asp His Ala Val Gly Asn Val Pro Glu Leu Ala
225                 230                 235                 240

Pro Ala Val Arg Tyr Leu Lys Gly Phe Ser Phe His Glu Phe Ala
                245                 250                 255

Glu Phe Thr Ala Glu Asp Val Gly Thr Ser Glu Ser Gly Leu Asn Ser
            260                 265                 270
```

```
Val Val Leu Ala Asn Asn Ser Glu Thr Val Leu Pro Leu Asn Glu
            275                 280                 285

Pro Val Tyr Gly Thr Lys Arg Lys Ser Gln Ile Glu Thr Tyr Leu Glu
        290                 295                 300

His Asn Glu Gly Ala Gly Val Gln His Leu Ala Leu Val Thr His Asp
305                 310                 315                 320

Ile Phe Thr Thr Leu Arg Glu Met Arg Lys Arg Ser Phe Leu Gly Gly
                325                 330                 335

Phe Glu Phe Met Pro Ser Pro Pro Thr Tyr Tyr Ala Asn Leu His
            340                 345                 350

Asn Arg Ala Ala Asp Val Leu Thr Val Asp Gln Ile Lys Gln Cys Glu
        355                 360                 365

Glu Leu Gly Ile Leu Val Asp Arg Asp Gln Gly Thr Leu Leu Gln
        370                 375                 380

Ile Phe Thr Lys Pro Val Gly Asp Arg Pro Thr Ile Phe Ile Glu Ile
385                 390                 395                 400

Ile Gln Arg Ile Gly Cys Met Val Glu Asp Glu Gly Lys Val Tyr
                405                 410                 415

Gln Lys Gly Ala Cys Gly Gly Phe Gly Lys Gly Asn Phe Ser Glu Leu
            420                 425                 430

Phe Lys Ser Ile Glu Glu Tyr Glu Lys Thr Leu Glu Ala Lys Arg Thr
            435                 440                 445

Ala

<210> SEQ ID NO 37
<211> LENGTH: 1614
<212> TYPE: DNA
<213> ORGANISM: Triticum aestivum

<400> SEQUENCE: 37
gcacgagcaa gaagcgaaca cacaccatgc cgcccacccc caccaccccc gcagccaccg      60
gcgccgccgc ggtgacgccg gagcacgcgc ggccgcgccg aatggtccgc ttcaacccgc     120
gcagcgaccg cttccacacg ctcgccttcc accacgtcga gttctggtgc gcggacgccg     180
cctccgccgc cggccgcttc gccttcgcgc tcggcgcgcc gctcgccgcc aggtccgacc     240
tctccacggg gaactccgtg cacgcctccc agctgctccg ctcgggcaac ctcgccttcc     300
tcttcacggc ccctacgcc aacgctgcg acgccgccac cgcctccctg ccctccttct     360
ccgccgacgc cgcgcgccag ttctccgcgg accacggcct cgcggtgcgc tccatagcgc     420
tgcgcgtcgc ggacgctgcc gaggccttcc gcgccagcgt cgacggggc gcgcgcccgg     480
ccttcagccc tgtggacctc ggccgcggct tcggcttcgc ggaggtcgag ctctacggcg     540
acgtcgtgct ccgcttcgtc agccaccccgg acggcaggga cgtgcccttc ttgccggggt     600
tcgagggcgt gagcaaccca gacgccgtgg actacgccct gacgcggttc gaccacgtcg     660
tcggcaacgt cccggagctt gccccgccg cggcctacgt cgccgggttc acggggttcc     720
acgagttcgc cgagttcacg acggaggacg tgggcacggc cgagagcggg ctcaactcga     780
tggtgctcgc caacaactcg gagggcgtgc tgctgccgct caacgagccg gtgcacggca     840
ccaagcgccg gagccagata cagacgttcc tggaacacca cggcggctcg ggcgtgcagc     900
acatcgcggt ggccagcagc gacgtgctca ggacgctcag ggagatgcgt gcgcgctccg     960
ccatgggcgc cttcgacttc ctgccacccc cgctgccgaa gtactacgaa ggcgtgcgg    1020
gcatcgccgg ggatgtgctc tcggaggcgc agatcaagga atgccaggag ctgggggtgc    1080
```

-continued

```
tcgtcgacag ggacgaccaa ggggtgttgc tacaaatctt caccaagcca gtaggggaca    1140
ggccgacgtt gttcctggag atgatccaga ggatcgggtg catggagaag gacgagagag    1200
gggaagagta ccagaagggt ggctgcggcg ggttcggcaa aggcaacttc tccgagctgt    1260
tcaagtccat tgaagattac gagaagtccc ttgaagccaa gcaatctgct gcagttcagg    1320
gatcatagga tagaagctgg agctggagga gctgatccag tactttgtat caggtctcat    1380
ggagcaaaag aaaatgatgt tgtttgtaag atgcggcgcg caattatgtc cgatgttata    1440
attggtgaag ctgaagacag atgtatccta tgtatgatgg gtgtaataga tggtagaggg    1500
ggctcggctc acacatgaac aaaatgtact gttggcattg ttgtataatc ttgcttgcaa    1560
gtaaaataaa gaagaaccga ttttgagttc tgcatcaaaa aaaaaaaaaa aaaa          1614
```

<210> SEQ ID NO 38
<211> LENGTH: 433
<212> TYPE: PRT
<213> ORGANISM: Triticum aestivum

<400> SEQUENCE: 38

```
Met Pro Pro Thr Pro Thr Thr Pro Ala Ala Thr Gly Ala Ala Ala Val
 1               5                  10                  15

Thr Pro Glu His Ala Arg Pro Arg Arg Met Val Arg Phe Asn Pro Arg
                20                  25                  30

Ser Asp Arg Phe His Thr Leu Ala Phe His His Val Glu Phe Trp Cys
            35                  40                  45

Ala Asp Ala Ala Ser Ala Ala Gly Arg Phe Ala Phe Ala Leu Gly Ala
        50                  55                  60

Pro Leu Ala Ala Arg Ser Asp Leu Ser Thr Gly Asn Ser Val His Ala
65                  70                  75                  80

Ser Gln Leu Leu Arg Ser Gly Asn Leu Ala Phe Leu Phe Thr Ala Pro
                85                  90                  95

Tyr Ala Asn Gly Cys Asp Ala Ala Thr Ala Ser Leu Pro Ser Phe Ser
            100                 105                 110

Ala Asp Ala Ala Arg Gln Phe Ser Ala Asp His Gly Leu Ala Val Arg
        115                 120                 125

Ser Ile Ala Leu Arg Val Ala Asp Ala Ala Glu Ala Phe Arg Ala Ser
    130                 135                 140

Val Asp Gly Gly Ala Arg Pro Ala Phe Ser Pro Val Asp Leu Gly Arg
145                 150                 155                 160

Gly Phe Gly Phe Ala Glu Val Glu Leu Tyr Gly Asp Val Val Leu Arg
                165                 170                 175

Phe Val Ser His Pro Asp Gly Arg Asp Val Pro Phe Leu Pro Gly Phe
            180                 185                 190

Glu Gly Val Ser Asn Pro Asp Ala Val Asp Tyr Gly Leu Thr Arg Phe
        195                 200                 205

Asp His Val Val Gly Asn Val Pro Glu Leu Ala Pro Ala Ala Ala Tyr
    210                 215                 220

Val Ala Gly Phe Thr Gly Phe His Glu Phe Ala Glu Phe Thr Thr Glu
225                 230                 235                 240

Asp Val Gly Thr Ala Glu Ser Gly Leu Asn Ser Met Val Leu Ala Asn
                245                 250                 255

Asn Ser Glu Gly Val Leu Leu Pro Leu Asn Glu Pro Val His Gly Thr
            260                 265                 270

Lys Arg Arg Ser Gln Ile Gln Thr Phe Leu Glu His His Gly Gly Ser
```

```
                275                 280                 285
Gly Val Gln His Ile Ala Val Ala Ser Ser Asp Val Leu Arg Thr Leu
    290                 295                 300
Arg Glu Met Arg Ala Arg Ser Ala Met Gly Gly Phe Asp Phe Leu Pro
305                 310                 315                 320
Pro Pro Leu Pro Lys Tyr Tyr Glu Gly Val Arg Arg Ile Ala Gly Asp
                325                 330                 335
Val Leu Ser Glu Ala Gln Ile Lys Glu Cys Gln Leu Gly Val Leu
    340                 345                 350
Val Asp Arg Asp Gln Gly Val Leu Leu Gln Ile Phe Thr Lys Pro
    355                 360                 365
Val Gly Asp Arg Pro Thr Leu Phe Leu Glu Met Ile Gln Arg Ile Gly
    370                 375                 380
Cys Met Glu Lys Asp Glu Arg Gly Glu Glu Tyr Gln Lys Gly Gly Cys
385                 390                 395                 400
Gly Gly Phe Gly Lys Gly Asn Phe Ser Glu Leu Phe Lys Ser Ile Glu
                405                 410                 415
Asp Tyr Glu Lys Ser Leu Glu Ala Lys Gln Ser Ala Ala Val Gln Gly
                420                 425                 430
Ser

<210> SEQ ID NO 39
<211> LENGTH: 317
<212> TYPE: PRT
<213> ORGANISM: Synechocystis sp.

<400> SEQUENCE: 39

Met Val Tyr His Val Arg Pro Lys His Ala Leu Phe Leu Ala Phe Tyr
 1               5                  10                  15
Cys Tyr Phe Ser Leu Leu Thr Met Ala Ser Ala Thr Ile Ala Ser Ala
                20                  25                  30
Asp Leu Tyr Glu Lys Ile Lys Asn Phe Tyr Asp Asp Ser Ser Gly Leu
            35                  40                  45
Trp Glu Asp Val Trp Gly Glu His Met His Gly Tyr Tyr Gly Pro
    50                  55                  60
His Gly Thr Tyr Arg Ile Asp Arg Arg Gln Ala Gln Ile Asp Leu Ile
65                  70                  75                  80
Lys Glu Leu Leu Ala Trp Ala Val Pro Gln Asn Ser Ala Lys Pro Arg
                85                  90                  95
Lys Ile Leu Asp Leu Gly Cys Gly Ile Gly Gly Ser Ser Leu Tyr Leu
                100                 105                 110
Ala Gln Gln His Gln Ala Glu Val Met Gly Ala Ser Leu Ser Pro Val
            115                 120                 125
Gln Val Glu Arg Ala Gly Glu Arg Ala Arg Ala Leu Gly Leu Gly Ser
    130                 135                 140
Thr Cys Gln Phe Gln Val Ala Asn Ala Leu Asp Leu Pro Phe Ala Ser
145                 150                 155                 160
Asp Ser Phe Asp Trp Val Trp Ser Leu Glu Ser Gly Glu His Met Pro
                165                 170                 175
Asn Lys Ala Gln Phe Leu Gln Glu Ala Trp Arg Val Leu Lys Pro Gly
                180                 185                 190
Gly Arg Leu Ile Leu Ala Thr Trp Cys His Arg Pro Ile Asp Pro Gly
            195                 200                 205
Asn Gly Pro Leu Thr Ala Asp Glu Arg Arg His Leu Gln Ala Ile Tyr
```

-continued

```
              210                 215                 220
Asp Val Tyr Cys Leu Pro Tyr Val Val Ser Leu Pro Asp Tyr Glu Ala
225                 230                 235                 240

Ile Ala Arg Glu Cys Gly Phe Gly Glu Ile Lys Thr Ala Asp Trp Ser
                245                 250                 255

Val Ala Val Ala Pro Phe Trp Asp Arg Val Ile Glu Ser Ala Phe Asp
                260                 265                 270

Pro Arg Val Leu Trp Ala Leu Gly Gln Ala Gly Pro Lys Ile Ile Asn
                275                 280                 285

Ala Ala Leu Cys Leu Arg Leu Met Lys Trp Gly Tyr Glu Arg Gly Leu
                290                 295                 300

Val Arg Phe Gly Leu Leu Thr Gly Ile Lys Pro Leu Val
305                 310                 315

<210> SEQ ID NO 40
<211> LENGTH: 348
<212> TYPE: PRT
<213> ORGANISM: Arabidopsis thaliana

<400> SEQUENCE: 40

Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
                20                  25                  30

Pro Ser Ser Ser Ser Val Ser Met Thr Thr Thr Arg Gly Asn Val
            35                  40                  45

Ala Val Ala Ala Ala Thr Ser Thr Glu Ala Leu Arg Lys Gly Ile
    50                  55                  60

Ala Glu Phe Tyr Asn Glu Thr Ser Gly Leu Trp Glu Ile Trp Gly
65              70                  75                  80

Asp His Met His His Gly Phe Tyr Asp Pro Asp Ser Ser Val Gln Leu
                85                  90                  95

Ser Asp Ser Gly His Lys Glu Ala Gln Ile Arg Met Ile Glu Glu Ser
                100                 105                 110

Leu Arg Phe Ala Gly Val Thr Asp Glu Glu Glu Lys Lys Ile Lys
        115                 120                 125

Lys Val Val Asp Val Gly Cys Gly Ile Gly Gly Ser Ser Arg Tyr Leu
    130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Gln Ser Leu Ser His
                165                 170                 175

Lys Ala Ser Phe Gln Val Ala Asp Ala Leu Asp Gln Pro Phe Glu Asp
                180                 185                 190

Gly Lys Phe Asp Leu Val Trp Ser Met Glu Ser Gly Glu His Met Pro
            195                 200                 205

Asp Lys Ala Lys Phe Val Lys Glu Leu Val Arg Val Ala Ala Pro Gly
    210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Asp Tyr Val Asn
                260                 265                 270
```

```
Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
        290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
        340                 345

<210> SEQ ID NO 41
<211> LENGTH: 434
<212> TYPE: PRT
<213> ORGANISM: Hordeum vulgare

<400> SEQUENCE: 41

Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu Phe Trp
        35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
    130                 135                 140

Ser Arg Arg Gly Ala Arg Pro Ala Phe Ala Pro Val Asp Leu Gly
145                 150                 155                 160

Arg Gly Phe Ala Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
        195                 200                 205

Phe Asp His Val Val Gly Asn Val Pro Glu Leu Ala Pro Ala Ala Ala
    210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Leu Ala
                245                 250                 255

Asn Asn Ser Glu Gly Val Leu Leu Pro Leu Asn Glu Pro Val His Gly
            260                 265                 270

Thr Lys Arg Arg Ser Gln Ile Gln Thr Phe Leu Glu His His Gly Gly
        275                 280                 285

Pro Gly Val Gln His Ile Ala Val Ala Ser Ser Asp Val Leu Arg Thr
    290                 295                 300
```

```
Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
                325                 330                 335

Asp Val Leu Ser Glu Ala Gln Ile Lys Glu Cys Gln Glu Leu Gly Val
                340                 345                 350

Leu Val Asp Arg Asp Asp Gln Gly Val Leu Leu Gln Ile Phe Thr Lys
            355                 360                 365

Pro Val Gly Asp Arg Pro Thr Leu Phe Leu Glu Met Ile Gln Arg Ile
        370                 375                 380

Gly Cys Met Glu Lys Asp Glu Arg Gly Glu Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Ala Val Gln
                420                 425                 430

Gly Ser
```

<210> SEQ ID NO 42
<211> LENGTH: 442
<212> TYPE: PRT
<213> ORGANISM: Daucus carota

<400> SEQUENCE: 42

```
Met Gly Lys Lys Gln Ser Glu Ala Glu Ile Leu Ser Ser Asn Ser Ser
1               5                   10                  15

Asn Thr Ser Pro Ala Thr Phe Lys Leu Val Gly Phe Asn Asn Phe Val
                20                  25                  30

Arg Ala Asn Pro Lys Ser Asp His Phe Ala Val Lys Arg Phe His His
            35                  40                  45

Ile Glu Phe Trp Cys Gly Asp Ala Thr Asn Thr Ser Arg Arg Phe Ser
    50                  55                  60

Trp Gly Leu Gly Met Pro Leu Ala Lys Ser Asp Leu Ser Thr Gly
65                  70                  75                  80

Asn Ser Val His Ala Ser Tyr Leu Val Arg Ser Ala Asn Leu Ser Phe
                85                  90                  95

Val Phe Thr Ala Pro Tyr Ser Pro Ser Thr Thr Ser Ser Gly Ser
                100                 105                 110

Ala Ala Ile Pro Ser Phe Ser Ala Ser Gly Phe His Ser Phe Ala Ala
            115                 120                 125

Lys His Gly Leu Ala Val Arg Ala Ile Ala Leu Glu Val Ala Asp Val
    130                 135                 140

Ala Ala Ala Phe Glu Ala Ser Val Ala Arg Gly Ala Arg Pro Ala Ser
145                 150                 155                 160

Ala Pro Val Glu Leu Asp Asp Gln Ala Trp Leu Ala Glu Val Glu Leu
                165                 170                 175

Tyr Gly Asp Val Val Leu Arg Phe Val Ser Phe Gly Arg Glu Glu Gly
                180                 185                 190

Leu Phe Leu Pro Gly Phe Glu Ala Val Glu Gly Thr Ala Ser Phe Pro
            195                 200                 205

Asp Leu Asp Tyr Gly Ile Arg Arg Leu Asp His Ala Val Gly Asn Val
    210                 215                 220

Thr Glu Leu Gly Pro Val Val Glu Tyr Ile Lys Gly Phe Thr Gly Phe
225                 230                 235                 240
```

-continued

```
His Glu Phe Ala Glu Phe Thr Ala Glu Asp Val Gly Thr Leu Glu Ser
            245                 250                 255

Gly Leu Asn Ser Val Val Leu Ala Asn Asn Glu Glu Met Val Leu Leu
        260                 265                 270

Pro Leu Asn Glu Pro Val Tyr Gly Thr Lys Arg Lys Ser Gln Ile Gln
    275                 280                 285

Thr Tyr Leu Glu His Asn Glu Gly Ala Gly Val Gln His Leu Ala Leu
290                 295                 300

Val Ser Glu Asp Ile Phe Arg Thr Leu Arg Glu Met Arg Lys Arg Ser
305                 310                 315                 320

Cys Leu Gly Gly Phe Glu Phe Met Pro Ser Pro Pro Thr Tyr Tyr
                325                 330                 335

Lys Asn Leu Lys Asn Arg Val Gly Asp Val Leu Ser Asp Glu Gln Ile
            340                 345                 350

Lys Glu Cys Glu Asp Leu Gly Ile Leu Val Asp Arg Asp Gln Gly
        355                 360                 365

Thr Leu Leu Gln Ile Phe Thr Lys Pro Val Gly Asp Arg Pro Thr Leu
    370                 375                 380

Phe Ile Glu Ile Ile Gln Arg Val Gly Cys Met Leu Lys Asp Asp Ala
385                 390                 395                 400

Gly Gln Met Tyr Gln Lys Gly Cys Gly Phe Gly Lys Gly Asn
                405                 410                 415

Phe Ser Glu Leu Phe Lys Ser Ile Glu Glu Tyr Glu Lys Thr Leu Glu
            420                 425                 430

Ala Lys Gln Ile Thr Gly Ser Ala Ala Ala
            435                 440

<210> SEQ ID NO 43
<211> LENGTH: 445
<212> TYPE: PRT
<213> ORGANISM: Arabidopsis thaliana

<400> SEQUENCE: 43

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
        35                  40                  45

His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
    130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
```

```
                    165                 170                 175
Ala Glu Val Lys Leu Tyr Gly Asp Val Val Leu Arg Tyr Val Ser Tyr
        180                 185                 190

Lys Ala Glu Asp Thr Glu Lys Ser Glu Phe Leu Pro Gly Phe Glu Arg
            195                 200                 205

Val Glu Asp Ala Ser Ser Phe Pro Leu Asp Tyr Gly Ile Arg Arg Leu
        210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
            245                 250                 255

Asp Val Gly Thr Ala Glu Ser Gly Leu Asn Ser Ala Val Leu Ala Ser
            260                 265                 270

Asn Asp Glu Met Val Leu Leu Pro Ile Asn Glu Pro Val His Gly Thr
        275                 280                 285

Lys Arg Lys Ser Gln Ile Gln Thr Tyr Leu Glu His Asn Glu Gly Ala
        290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
            325                 330                 335

Ser Pro Pro Thr Tyr Tyr Gln Asn Leu Lys Lys Arg Val Gly Asp
        340                 345                 350

Val Leu Ser Asp Gln Ile Lys Glu Cys Glu Glu Leu Gly Ile Leu
        355                 360                 365

Val Asp Arg Asp Gln Gly Thr Leu Leu Gln Ile Phe Thr Lys Pro
        370                 375                 380

Leu Gly Asp Arg Pro Thr Ile Phe Ile Glu Ile Ile Gln Arg Val Gly
385                 390                 395                 400

Cys Met Met Lys Asp Glu Gly Lys Ala Tyr Gln Ser Gly Gly Cys
            405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
        435                 440                 445
```

<210> SEQ ID NO 44
<211> LENGTH: 60
<212> TYPE: DNA
<213> ORGANISM: Artificial Sequence
<220> FEATURE:
<223> OTHER INFORMATION: Primer

<400> SEQUENCE: 44
agcgcggccg catggccacc gtggtgagga tcccaacaat ctcatgcatc cacatccaca        60

<210> SEQ ID NO 45
<211> LENGTH: 36
<212> TYPE: DNA
<213> ORGANISM: Artificial Sequence
<220> FEATURE:
<223> OTHER INFORMATION: Primer

<400> SEQUENCE: 45
agcgcggccg cttatctagt gtggaaataa tgatca        36